United States Patent
Katayama et al.

(10) Patent No.: US 10,054,855 B2
(45) Date of Patent: Aug. 21, 2018

(54) CHEMICALLY AMPLIFIED POSITIVE-TYPE PHOTOSENSITIVE RESIN COMPOSITION

(71) Applicant: TOKYO OHKA KOGYO CO., LTD., Kawasaki-shi (JP)

(72) Inventors: Shota Katayama, Kanagawa (JP); Aya Momozawa, Kanagawa (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 232 days.

(21) Appl. No.: 15/074,124

(22) Filed: Mar. 18, 2016

(65) Prior Publication Data

US 2016/0291469 A1 Oct. 6, 2016

(30) Foreign Application Priority Data

Mar. 31, 2015 (JP) ................. 2015-073703

(51) Int. Cl.
| | | |
|---|---|---|
| G03F 7/004 | (2006.01) | |
| G03F 7/039 | (2006.01) | |
| G03F 7/038 | (2006.01) | |
| G03F 7/16 | (2006.01) | |
| C08F 220/24 | (2006.01) | |
| C08F 220/18 | (2006.01) | |
| C08F 220/22 | (2006.01) | |
| C08F 220/28 | (2006.01) | |
| H01L 21/027 | (2006.01) | |
| H01L 21/033 | (2006.01) | |
| H01L 21/311 | (2006.01) | |

(52) U.S. Cl.
CPC .......... *G03F 7/0397* (2013.01); *C08F 220/18* (2013.01); *C08F 220/22* (2013.01); *C08F 220/24* (2013.01); *C08F 220/28* (2013.01); *G03F 7/004* (2013.01); *G03F 7/0046* (2013.01); *G03F 7/0382* (2013.01); *G03F 7/0392* (2013.01); *G03F 7/162* (2013.01); *G03F 7/168* (2013.01); *H01L 21/0274* (2013.01); *H01L 21/0337* (2013.01); *H01L 21/31116* (2013.01); *C07C 2603/18* (2017.05)

(58) Field of Classification Search
CPC ...... G03F 7/004; G03F 7/0046; G03F 7/0382; G03F 7/0392; G03F 7/0397; G03F 7/40; G03F 7/162; G03F 7/168; C08F 220/18; C08F 220/24; C08F 220/28; C08F 220/22; H01L 21/0274; H01L 21/0337; H01L 21/31116; C07C 2603/18
USPC ............ 430/270.1, 322, 325, 329, 330, 331; 526/243, 281, 245; 568/817
See application file for complete search history.

(56) References Cited

U.S. PATENT DOCUMENTS

| | | | | |
|---|---|---|---|---|
| 6,080,522 A | * | 6/2000 | Ito ........................ | C08G 61/02 430/165 |
| 2004/0097707 A1 | * | 5/2004 | Lee ....................... | C07K 14/705 530/350 |
| 2008/0032231 A1 | * | 2/2008 | Hatakeyama ........... | G03F 7/094 430/270.1 |
| 2012/0184101 A1 | * | 7/2012 | Yasuda .................. | G03F 7/0392 438/676 |
| 2013/0026044 A1 | * | 1/2013 | Yasuda .................. | G03F 7/0392 205/136 |
| 2013/0337380 A1 | * | 12/2013 | Liu ......................... | G03F 7/004 430/285.1 |
| 2015/0355543 A1 | * | 12/2015 | Takemura ............. | G03F 7/0392 430/270.1 |
| 2016/0280621 A1 | * | 9/2016 | Yokokawa ............. | C07C 41/09 |

FOREIGN PATENT DOCUMENTS

| | | | |
|---|---|---|---|
| JP | H09-176112 | | 7/1997 |
| JP | H11-052562 | | 2/1999 |
| JP | 2005232112 A | * | 9/2005 |
| JP | 2007017867 A | * | 1/2007 |
| JP | 2009244803 A | * | 10/2009 |
| JP | 2012108182 A | * | 6/2012 |

OTHER PUBLICATIONS

Machine Translation of JP 2009-244803 (no date).*
Machine Translation of JP2005-232112 (no date).*
Machine Translation of JP2007-017867 (no date).*

* cited by examiner

*Primary Examiner* — Amanda C Walke
(74) *Attorney, Agent, or Firm* — Knobbe Martens Olson & Bear LLP

(57) ABSTRACT

A photosensitive resin composition, a method of manufacturing a substrate with a template using the composition, and a method of manufacturing a plated article using the substrate with a template. The photosensitive resin composition may be used to form a plated article on a metal surface of a substrate The composition includes an acid generator that, when irradiated with an active ray or radiation, generates an acid, a resin that, under an action of an acid, undergoes an increase in solubility thereof in alkali, and a fluorene compound represented by the formula (1).

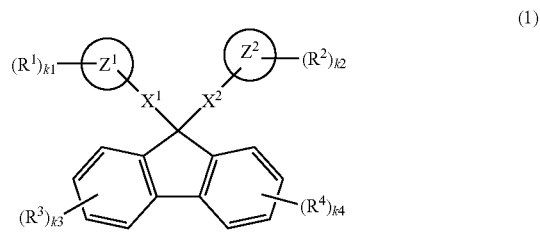

(1)

18 Claims, No Drawings

CHEMICALLY AMPLIFIED POSITIVE-TYPE PHOTOSENSITIVE RESIN COMPOSITION

This application claims priority to Japanese Patent Application No. 2015-073703, filed Mar. 31, 2015, the content of which is incorporated herein by reference.

BACKGROUND OF THE INVENTION

Field of the Invention

The present invention relates to a chemically amplified positive-type photosensitive resin composition, a method of manufacturing a substrate with a template by using the above chemically amplified positive-type photosensitive resin composition, and a method of manufacturing a plated article by using the above substrate with the template.

Related Art

Photofabrication is now the mainstream precision microfabrication technique. Photofabrication is a generic term describing the technology used for manufacturing a wide variety of precision components such as semiconductor packages. The manufacturing is carried out by applying a photoresist composition to the surface of a processing target to form a photoresist layer, patterning this photoresist layer using photolithographic techniques, and then conducting chemical etching, electrolytic etching, and/or electroforming based mainly on electroplating, using the patterned photoresist layer (photoresist pattern) as a mask.

In recent years, high density packaging technologies for semiconductor packages have progressed in association with downsizing of electronics devices, and the increase in package density has been developed on the basis of mounting multi-pin thin film in packages, miniaturizing of package size, two-dimensional packaging technologies or three-dimensional packaging technologies by a flip-chip method. In these types of high density packaging technologies, connection terminals such as: protruding electrodes (mounting terminals) known as bumps protruding above the package; or metal posts connecting rewiring, which extends from peripheral terminals on a wafer, with the mounting terminals, are disposed on the surface of the substrate with high precision.

A photoresist composition is used in the photofabrication as described above. Chemically amplified photoresist compositions containing an acid generator has been known as such photoresist compositions (see, for example, Patent Documents 1 and 2). According to the chemically amplified photoresist composition, an acid is generated from the acid generator upon irradiation with radiation (exposure) and diffusion of the acid is promoted through heat treatment to cause an acid catalytic reaction with a base resin and the like in the composition, resulting in a change in the alkali-solubility thereof.

These chemically amplified positive-type photoresist compositions are used for forming, for example, plated articles such as bumps and metal posts by a plating process. Specifically, a photoresist layer having a desired film thickness is formed on a support such as a metal substrate with a chemically amplified photoresist composition, and the photoresist layer is exposed through a predetermined mask pattern and then developed to form a photoresist pattern used as a template in which portions for forming bumps and metal posts have been selectively removed (stripped). Then, bumps and metal posts can be formed by embedding a conductor such as copper into the removed portions (non-resist sections) by plating, and then removing the surrounding residual resist pattern.

Patent Document 1: Japanese Unexamined Patent Application, Publication No. H09-176112
Patent Document 2: Japanese Unexamined Patent Application, Publication No. H11-52562

SUMMARY OF THE INVENTION

The increase in demand for high-density packaging has made it necessary to enhance the degree of refining patterns and to increase film thickness.

An exposure device having a higher lens numerical aperture (NA) is used for pattern refining in some cases. However, when exposure is carried out with an exposure device having a high lens numerical aperture, deterioration in shape, which is supposed to derive from a difference in optical density, may occur in a resist pattern having a high film thickness.

As disclosed in Patent Documents 1 and 2, when a resist pattern that serves as a template for the formation of bumps, metal posts, etc. is formed on a metal substrate using a conventionally known chemically amplified positive-type photoresist composition, it is difficult to form a resist pattern that does not cause a deterioration in a sectional shape of a non-resist section of the resist pattern.

The present invention has been made in view of the above problems, and an object of the present invention is to provide a chemically amplified positive-type photosensitive resin composition that, even when an exposure device having a high lens numerical aperture (NA) is used in the formation of a resist pattern served as a template for a plated article on a substrate using a chemically amplified positive-type photosensitive resin composition, can suppress a deterioration in a sectional shape of a non-resist section of the resist pattern; a method of manufacturing a substrate with a template using the photosensitive resin composition; and a method of manufacturing a plated article using the substrate with a template.

The present inventors have made extensive and intensive studies with a view to attaining the above object and, as a result, have found that the above problem can be solved by incorporating a fluorene compound having a specific structure into a chemically amplified positive-type photosensitive resin composition. This has led to the completion of the present invention. Specifically, the present invention provides the following.

A first aspect of the present invention is a chemically amplified positive-type photosensitive resin composition used for creating a plated article on a metal surface of a substrate having a metal surface, comprising an (A) acid generator that, when irradiated with an active ray or radiation, generates an acid; a (B) resin, under an action of an acid, undergoes an increase in solubility thereof in alkali; and a (C) fluorene compound represented by the following formula (1).

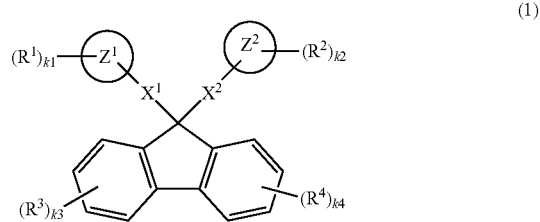

(1)

wherein each of ring Z¹ and ring Z² independently represents a benzene ring or a naphthalene ring; each of X¹ and X² independently represents a single bond or —S—; each of R¹, R², R³, and R⁴ independently represents a monovalent hydrocarbon group, a hydroxyl group, a (meth)acryloyloxy group, a group represented by —OR$^{4a}$, a group represented by —SR$^{4b}$, an acyl group, an alkoxycarbonyl group, a halogen atom, a nitro group, a cyano group, a mercapto group, a carboxy group, an amino group, a carbamoyl group, a group represented by —NHR$^{4c}$, a group represented by —N(R$^{4d}$)$_2$, a (meth)acryloyloxy group, a sulfo group, or a group in which at least a part of the hydrogen atoms bonded to a carbon atom contained in a monovalent hydrocarbon group, a group represented by —OR$^{4a}$, a group represented by —SR$^{4b}$, an acyl group, an alkoxycarbonyl group, a group represented by —NHR$^{4c}$, or a group represented by —N(R$^{4d}$)$_2$) is substituted by a monovalent hydrocarbon group, a hydroxyl group, a group represented by —OR$^{4a}$, a group represented by —SR$^{4b}$, an acyl group, an alkoxycarbonyl group, a halogen atom, a nitro group, a cyano group, a mercapto group, a carboxy group, an amino group, a carbamoyl group, a group represented by —NHR$^{4c}$, a group represented by —N(R$^{4d}$)$_2$, a (meth)acryloyloxy group, a mesyloxy group, or a sulfo group; each of R$^{4a}$ to R$^{4d}$ independently represents a monovalent hydrocarbon group; and each of k1, k2, k3, and k4 independently represents an integer of 0 to 4.

A second aspect of the present invention is a method of manufacturing a substrate with a template, the method comprising: a lamination step of laminating a photosensitive resin layer consisting of the chemically amplified positive-type photosensitive resin composition according to the first aspect on a metal surface of a substrate having a metal surface;

an exposure step of irradiating the photosensitive resin layer with an active ray or radiation; and a development step of developing the photosensitive resin layer after the exposure to form a template for forming a plated article.

A third aspect of the present invention is a method of manufacturing a plated article, the method comprising: plating the substrate with the template manufactured by the method according to the second aspect to form the plated article within the template.

The present invention can provide a chemically amplified positive-type photosensitive resin composition that, even when an exposure device having a high lens numerical aperture (NA) is used in the formation of a resist pattern served as a template for a plated article on a substrate using a chemically amplified positive-type photosensitive resin composition, can suppress a deterioration in a sectional shape of a non-resist section of the resist pattern; a method of manufacturing a substrate with a template using the photosensitive resin composition; and a method of manufacturing a plated article using the substrate with a template.

DETAILED DESCRIPTION OF THE INVENTION

<<Chemically Amplified Positive-Type Photosensitive Resin Composition>>

The chemically amplified positive-type photosensitive resin composition (hereinafter referred to also as "photosensitive resin composition") according to the present invention is a photosensitive resin composition for use in the formation of a plated article on a metal surface of a substrate having a metal surface, the composition comprising: an (A) acid generator that, when irradiated with an active ray or radiation, generates an acid (hereinafter referred to also as an "(A) acid generator"); a (B) resin that, under an action of an acid, undergoes an increase in solubility thereof in alkali (hereinafter referred to also as a "(B) resin"); and a (C) fluorene compound represented by the formula (1) (hereinafter referred to also as a "(C) fluorene compound"). The photosensitive resin composition may comprise a component such as a (D) alkali soluble resin, an (E) acid diffusion suppressing agent and an (S) organic solvent, if desired.

There is no particular limitation for the film thickness of a resist pattern formed with the photosensitive resin composition; however the photosensitive resin composition is preferably used for forming a thick resist pattern. The film thickness of a resist pattern formed with the photosensitive resin composition is preferably 10 μm or more, more preferably 10 to 150 μm, particularly preferably 20 to 120 μm, and most preferably 20 to 80 μm.

Described hereafter are essential or optional components of the photosensitive resin composition, and a method of manufacturing the photosensitive resin composition.

<(A) Acid Generator>

The (A) acid generator is a compound capable of generating an acid when irradiated with an active ray or radiation, and is not particularly limited as long as it is a compound which directly or indirectly generates an acid under the action of light. The (A) acid generator is preferably any one of the acid generators of the first to fifth aspects that will be described below. Hereinafter, preferred examples of the (A) acid generators that are suitably used in the photosensitive resin composition will be described as the first to fifth aspects.

The first aspect of the (A) acid generator may be a compound represented by the following formula (a1).

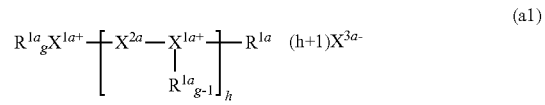

In the formula (a1), $X^{1a}$ represents a sulfur atom or iodine atom having a valence of g; g being 1 or 2. h represents the number of repeating units in the structure in parentheses. $R^{1a}$ represents an organic group that is bonded to $X^{1a}$, and represents an aryl group having 6 to 30 carbon atoms, a heterocyclic group having 4 to 30 carbon atoms, an alkyl group having 1 to 30 carbon atoms, an alkenyl group having 2 to 30 carbon atoms, or an alkynyl group having 2 to 30 carbon atoms, and $R^{1a}$ may be substituted by at least one selected from the group consisting of an alkyl group, a hydroxyl group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic group, an aryloxy group, an alkylsulfinyl group, an arylsulfinyl group, an alkylsulfonyl group, an arylsulfonyl group, an alkyleneoxy group, an amino group, a cyano group, a nitro group, and halogen atoms. The number of $R^{1a}$s is g+h (g−1)+1, and the $R^{1a}$s may be either identical to or different from each other. Furthermore, two or more $R^{1a}$s may be bonded to each other directly or via —O—, —S—, —SO—, —SO$_2$—, —NH—, —NR$^{2a}$—, —CO—, —COO—, —CONH—, an alkylene group having 1 to 3 carbon atoms, or a phenylene group, and may form a ring structure containing $X^{1a}$. $R^{2a}$ represents an alkyl group having 1 to 5 carbon atoms, or an aryl group having 6 to 10 carbon atoms.

$X^{2a}$ has a structure represented by the following formula (a2).

In the formula (a2), $X^{4a}$ represents an alkylene group having 1 to 8 carbon atoms, an arylene group having 6 to 20 carbon atoms, or a divalent group of a heterocyclic compound having 8 to 20 carbon atoms, and $X^{4a}$ may be substituted by at least one selected from the group consisting of an alkyl group having 1 to 8 carbon atoms, an alkoxy group having 1 to 8 carbon atoms, an aryl group having 6 to 10 carbon atoms, a hydroxyl group, a cyano group, a nitro group, and halogen atoms. $X^{5a}$ represents —O—, —S—, —SO—, —SO$_2$—, —NH—, —NR$^{2a}$—, —CO—, —COO—, —CONH—, an alkylene group having 1 to 3 carbon atoms, or a phenylene group. h represents the number of repeating units of the structure in parentheses. h+1 $X^{4a}$s and h $X^{5a}$s may be either identical to or different from each other. $R^{2a}$ has the same definition as described above.

$X^{3a-}$ represents a counterion of an onium, and examples thereof include a fluorinated alkylfluorophosphoric acid anion represented by the following formula (a17) or a borate anion represented by the following formula (a18).

$$[(R^{3a})PF_{6-j}]^-  \quad (a17)$$

In the formula (a17), $R^{3a}$ represents an alkyl group with 80% or more of the hydrogen atoms being substituted by fluorine atoms. j represents the number of $R^{3a}$s and is an integer of 1 to 5. j $R^{3a}$s may be either identical to or different from each other.

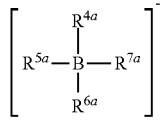

(a18)

In the formula (a18), each of $R^{4a}$ to $R^{7a}$ independently represents a fluorine atom or a phenyl group, and a part or all of the hydrogen atoms of the phenyl group may be substituted by at least one selected from the group consisting of a fluorine atom and a trifluoromethyl group.

Examples of the onium ion in the compound represented by the formula (a1) include triphenylsulfonium, tri-p-tolylsulfonium, 4-(phenylthio)phenyldiphenylsulfonium, bis[4-(diphenylsulfonio)phenyl] sulfide, bis[4-{bis[4-(2-hydroxyethoxy)phenyl]sulfonio}phenyl] sulfide, bis{4-[bis(4-fluorophenyl) sulfonio]phenyl} sulfide, 4-(4-benzoyl-2-chlorophenylthio)phenylbis(4-fluorophenyl)sulfonium, 7-isopropyl-9-oxo-10-thia-9,10-dihydroanthracene-2-yldi-p-tolylsulfonium, 7-isopropyl-9-oxo-10-thia-9,10-dihydroanthracene-2-yldiphenylsulfonium, 2-[(diphenyl)sulfonio]thioxanthone, 4-[4-(4-tert-butylbenzoyl)phenylthio]phenyldi-p-tolylsulfonium, 4-(4-benzoylphenylthio)phenyldiphenylsulfonium, diphenylphenacylsulfonium, 4-hydroxyphenylmethylbenzylsulfonium, 2-naphthylmethyl(1-ethoxycarbonyl)ethylsulfonium, 4-hydroxyphenylmethylphenacylsulfonium, phenyl[4-(4-biphenylthio)phenyl]-4-biphenylsulfonium, phenyl[4-(4-biphenylthio)phenyl]-3-biphenylsulfonium, [4-(4-acetophenylthio)phenyl]diphenylsulfonium, octadecylmethylphenacylsulfonium, diphenyliodonium, di-p-tolyliodonium, bis(4-dodecylphenyl)iodonium, bis(4-methoxyphenyl)iodonium, (4-octyloxyphenyl)phenyliodonium, bis(4-decyloxy)phenyliodonium, 4-(2-hydroxytetradecyloxy)phenylphenyliodonium, 4-isopropylphenyl(p-tolyl)iodonium, and 4-isobutylphenyl(p-tolyl)iodonium.

Among the onium ions in the compound represented by the formula (a1), a preferred onium ion may be a sulfonium ion represented by the following formula (a19).

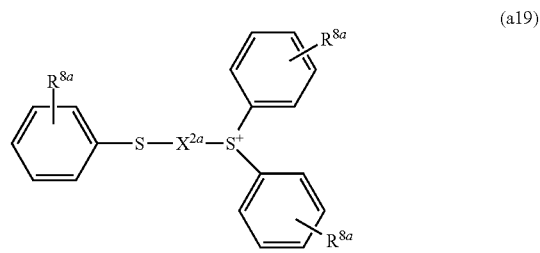

In the formula (a19), each $R^{8a}$ independently represents a hydrogen atom or a group selected from the group consisting of alkyl, hydroxy, alkoxy, alkylcarbonyl, alkylcarbonyloxy, alkyloxycarbonyl, a halogen atom, an aryl, which can be substituted, and arylcarbonyl. $X^{2a}$ has the same meaning as $X^{2a}$ in the formula (a1).

Specific examples of the sulfonium ion represented by the formula (a19) include 4-(phenylthio)phenyldiphenylsulfonium, 4-(4-benzoyl-2-chlorophenylthio)phenylbis(4-fluorophenyl)sulfonium, 4-(4-benzoylphenylthio)phenyldiphenylsulfonium, phenyl[4-(4-biphenylthio)phenyl]-4-biphenylsulfonium, phenyl[4-(4-biphenylthio)phenyl]-3-biphenylsulfonium, [4-(4-acetophenylthio)phenyl]diphenylsulfonium, and diphenyl[4-(p-terphenylthio)phenyl]diphenylsulfonium.

In regard to the fluorinated alkylfluorophosphoric acid anion represented by the formula (a17), $R^{3a}$ represents an alkyl group substituted by a fluorine atom, and a preferred number of carbon atoms is 1 to 8, while a more preferred number of carbon atoms is 1 to 4. Specific examples of the alkyl group include linear alkyl groups such as methyl, ethyl, propyl, butyl, pentyl and octyl; branched alkyl groups such as isopropyl, isobutyl, sec-butyl and tert-butyl; and cycloalkyl groups such as cyclopropyl, cyclobutyl, cyclopentyl, and cyclohexyl. The proportion of hydrogen atoms substituted by fluorine atoms in the alkyl groups is usually 80% or more, preferably 90% or more, and even more preferably 100%. If the substitution ratio of fluorine atoms is less than 80%, the acid strength of the onium fluorinated alkylfluorophosphate represented by the formula (a1) decreases.

A particularly preferred example of $R^{3a}$ is a linear or branched perfluoroalkyl group having 1 to 4 carbon atoms and a substitution ratio of fluorine atoms of 100%. Specific examples thereof include $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)CF$, and $(CF_3)_3C$. j, which is the number of $R^{3a}$s, represents an integer of 1 to 5, preferably 2 to 4, and particularly preferably 2 or 3.

Preferred specific examples of the fluorinated alkylfluorophosphoric acid anion include $[(CF_3CF_2)_2PF_4]^+$, $[(CF_3CF_2)_3PF_3]^-$, $[((CF_3)_2CF)_2PF_4]^-$, $[((CF_3)_2CF)_3PF_3]^-$, $[(CF_3CF_2CF_2)_2PF_4]^-$, $[(CF_3CF_2CF_2)_3PF_3]^-$, $[((CF_3)_2CFCF_2)_2PF_4]^-$, $[((CF_3)_2CFCF_2)_3PF_3]^-$, $[(CF_3CF_2CF_2CF_2)_2PF_4]^-$, and $[(CF_3CF_2CF_2)_3PF_3]^-$. Among these, $[(CF_3CF_2)_3$ PF$_3$]$^-$, [(CF$_3$CF$_2$CF$_2$)$_3$PF$_3$]$^-$, [((CF$_3$)$_2$CF)$_3$PF$_3$]$^-$, [((CF$_3$)$_2$CF)$_2$PF$_4$]$^-$, [((CF$_3$)$_2$CFCF$_2$)$_3$PF$_3$]$^-$, and [((CF$_3$)$_2$CFCF$_2$)$_2$PF$_4$]$^-$ are particularly preferred.

Preferred specific examples of the borate anion represented by the formula (a18) include tetrakis(pentafluorophenyl)borate ([B(C$_6$F$_5$)$_4$]$^-$), tetrakis[(trifluoromethyl)phenyl]borate ([B(C$_6$H$_4$CF$_3$)$_4$]$^-$), difluorobis(pentafluorophenyl)borate ([(C$_6$F$_5$)$_2$BF$_2$]$^-$), trifluoro(pentafluorophenyl)borate ([(C$_6$F$_5$)BF$_3$]$^-$), and tetrakis(difluorophenyl)borate ([B(C$_6$H$_3$F$_2$)$_4$]$^-$). Among these, tetrakis(pentafluorophenyl)borate ([B(C$_6$F$_5$)$_4$]$^-$) is particularly preferred.

The second aspect of the (A) acid generator includes halogen-containing triazine compounds such as 2,4-bis(trichloromethyl)-6-piperonyl-1,3,5-triazine, 2,4-bis(trichloromethyl)-6-[2-(2-furyl)ethenyl]-s-triazine, 2,4-bis(trichloromethyl)-6-[2-(5-methyl-2-furyl)ethenyl]-s-triazine, 2,4-bis(trichloromethyl)-6-[2-(5-ethyl-2-furyl)ethenyl]-s-triazine, 2,4-bis(trichloromethyl)-6-[2-(5-propyl-2-furyl)ethenyl]-s-triazine, 2,4-bis(trichloromethyl)-6-[2-(3,5-dimethoxyphenyl)ethenyl]-s-triazine, 2,4-bis(trichloromethyl)-6-[2-(3,5-diethoxyphenyl)ethenyl]-s-triazine, 2,4-bis(trichloromethyl)-6-[2-(3,5-dipropoxyphenyl)ethenyl]-s-triazine, 2,4-bis(trichloromethyl)-6-[2-(3-methoxy-5-ethoxyphenyl)ethenyl]-s-triazine, 2,4-bis(trichloromethyl)-6-[2-(3-methoxy-5-propoxyphenyl)ethenyl]-s-triazine, 2,4-bis(trichloromethyl)-6-[2-(3,4-methylenedioxyphenyl)ethenyl]-s-triazine, 2,4-bis(trichloromethyl)-6-(3,4-methylenedioxyphenyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(2-bromo-4-methoxy)styrylphenyl-s-triazine, 2,4-bis-trichloromethyl-6-(3-bromo-4-methoxy)styrylphenyl-s-triazine, 2-(4-methoxyphenyl)-4,6-bis(trichloromethyl)-1,3,5-triazine, 2-(4-methoxynaphthyl)-4,6-bis(trichloromethyl)-1,3,5-triazine, 2-[2-(2-furyl)ethenyl]-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl]-4,6-bis(trichloromethyl)-1,3,5-triazine, 2-[2-(3,4-dimethoxyphenyl)ethenyl]-4,6-bis(trichloromethyl)-1,3,5-triazine, 2-(3,4-methylenedioxyphenyl)-4,6-bis(trichloromethyl)-1,3,5-triazine, tris(1,3-dibromopropyl)-1,3,5-triazine and tris(2,3-dibromopropyl)-1,3,5-triazine, and halogen-containing triazine compounds represented by the following formula (a3) such as tris(2,3-dibromopropyl)isocyanurate.

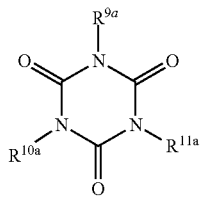

(a3)

In the formula (a3), each of R$^{9a}$, R$^{10a}$ and R$^{11a}$ independently represents a halogenated alkyl group.

Further, examples of the third aspect of the (A) acid generator include α-(p-toluenesulfonyloxyimino)-phenylacetonitrile, α-(benzenesulfonyloxyimino)-2,4-dichlorophenylacetonitrile, α-(benzenesulfonyloxyimino)-2,6-dichlorophenylacetonitrile, α-(2-chlorobenzenesulfonyloxyimino)-4-methoxyphenylacetonitrile and α-(ethylsulfonyloxyimino)-1-cyclopentenylacetonitrile, and compounds represented by the following formula (a4) having an oximesulfonate group.

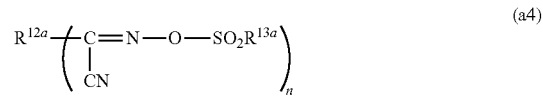

(a4)

In the formula (a4), R$^{12a}$ represents a monovalent, bivalent or trivalent organic group, R$^{13a}$ represents a substituted or unsubstituted saturated hydrocarbon group, an unsaturated hydrocarbon group, or an aromatic compound group, and n represents the number of repeating units of the structure in the parentheses.

In the formula (a4), the aromatic compound group indicates a group of compounds having physical and chemical properties characteristic of aromatic compounds, and examples thereof include aryl groups such as a phenyl group and a naphthyl group, and heteroaryl groups such as a furyl group and a thienyl group. These may have one or more appropriate substituents such as halogen atoms, alkyl groups, alkoxy groups and nitro groups on the rings. It is particularly preferable that R$^{13a}$ is an alkyl group having 1 to 6 carbon atoms such as a methyl group, an ethyl group, a propyl group, and a butyl group. In particular, compounds in which R$^{12a}$ represents an aromatic compound group, and R$^{13a}$ represents an alkyl group having 1 to 4 carbon atoms are preferred.

Examples of the acid generator represented by the formula (a4) include compounds in which R$^{12a}$ is any one of a phenyl group, a methylphenyl group and a methoxyphenyl group, and R$^{13a}$ is a methyl group, provided that n is 1, and specific examples thereof include α-(methylsulfonyloxyimino)-1-phenylacetonitrile, α-(methylsulfonyloxyimino)-1-(p-methylphenyl)acetonitrile, α-(methylsulfonyloxyimino)-1-(p-methoxyphenyl)acetonitrile, [2-(propylsulfonyloxyimino)-2,3-dihydroxythiophene-3-ylidene](o-tolyl)acetonitrile and the like. When n=2, the acid generator represented by the formula (a4) is specifically an acid generator represented by the following formula.

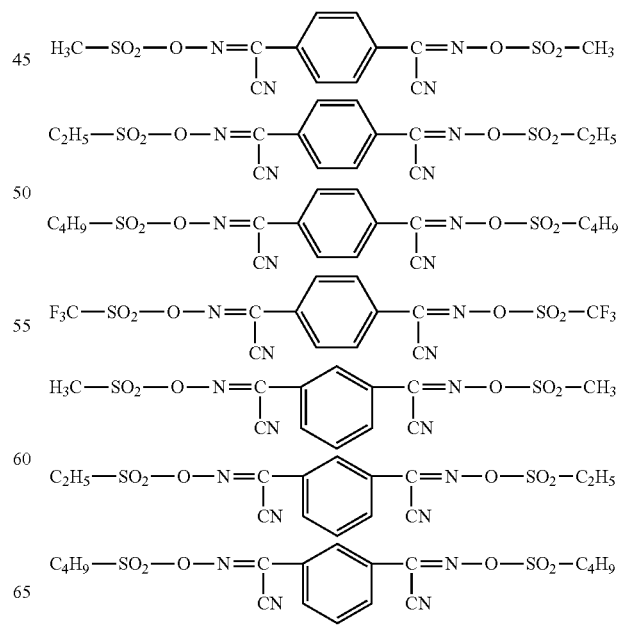

-continued

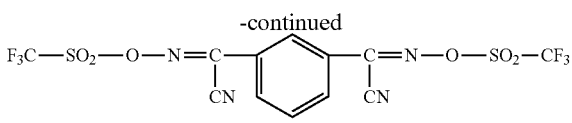

In addition, examples of the fourth aspect of the (A) acid generator include onium salts that have a naphthalene ring at their cation moiety. The expression "have a naphthalene ring" indicates having a structure derived from naphthalene and also indicates at least two ring structures and that their aromatic properties are maintained. The naphthalene ring may have a substituent such as a linear or branched alkyl group having 1 to 6 carbon atoms, a hydroxyl group, a linear or branched alkoxy group having 1 to 6 carbon atoms or the like. The structure derived from the naphthalene ring may be of a monovalent group (one free valance) or of a bivalent group (two free valences) or more, and is desirably of a monovalent group (in this regard, the number of free valance is counted except for the portions connecting with the substituents described above). The number of naphthalene rings is preferably 1 to 3.

Preferably, the cation moiety of the onium salt having a naphthalene ring at the cation moiety is of the structure represented by the following formula (a5).

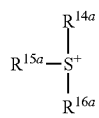
(a5)

In the formula (a5), at least one of $R^{14a}$, $R^{15a}$ and $R^{16a}$ represents a group represented by the following formula (a6), and the remaining represents a linear or branched alkyl group having 1 to 6 carbon atoms, a phenyl group which may have a substituent, a hydroxyl group, or a linear or branched alkoxy group having 1 to 6 carbon atoms. Alternatively, one of $R^{14a}$, $R^{15a}$ and $R^{16a}$ is a group represented by the following formula (a6), and each of the remaining two is independently a linear or branched alkylene group having 1 to 6 carbon atoms, and these terminals may bond to form a ring structure.

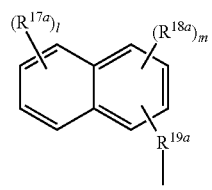
(a6)

In the formula (a6), each of $R^{17a}$ and $R^{18a}$ independently represents a hydroxyl group, a linear or branched alkoxy group having 1 to 6 carbon atoms, or a linear or branched alkyl group having 1 to 6 carbon atoms, and $R^{19a}$ represents a single bond or a linear or branched alkylene group having 1 to 6 carbon atoms that may have a substituent. Each of l and m independently represents an integer of 0 to 2, with the total of l and m being no greater than 3. In this regard, when there exists a plurality of $R^{17a}$, they may be identical to or different from each other. Furthermore, when there exists a plurality of $R^{18a}$, they may be identical to or different from each other.

Preferably, among $R^{14a}$, $R^{15a}$ and $R^{16a}$, the number of groups represented by the formula (a6) is 1 in view of the stability of the compound, and the remaining are linear or branched alkylene groups having 1 to 6 carbon atoms of which the terminals may bond to form a ring. In this case, the two alkylene groups described above compose a 3 to 9 membered ring including sulfur atom(s). Preferably, the number of atoms composing the ring (including sulfur atom(s)) is 5 or 6.

The substituent which can be introduced into the alkylene group is exemplified by an oxygen atom (in this case, a carbonyl group is formed along with a carbon atom that constitutes the alkylene group), a hydroxyl group or the like.

The substituent which can be introduced into the phenyl group is exemplified by a hydroxyl group, a linear or branched alkoxy group having 1 to 6 carbon atoms, a linear or branched alkyl group having 1 to 6 carbon atoms, or the like.

Examples of a suitable cation moiety include those represented by the following formulae (a7) and (a8), and the structure represented by the following formula (a8) is particularly preferable.

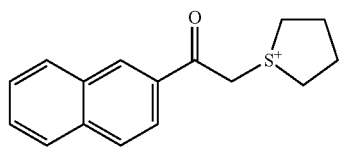
(a7)

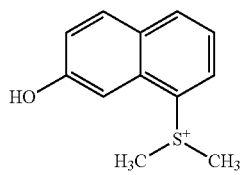
(a8)

The cation moieties may be of an iodonium salt or a sulfonium salt and are desirably of a sulfonium salt in view of acid-generating efficiency.

It is, therefore, desirable that the preferable anion moiety of the onium salt having a naphthalene ring at the cation moiety is an anion capable of forming a sulfonium salt.

The anion moiety of the acid generator is exemplified by fluoroalkylsulfonic acid ions, of which hydrogen atom(s) are partially or entirely fluorinated, or aryl sulfonic acid ions.

The alkyl group of the fluoroalkylsulfonic acid ions may be linear, branched or cyclic and have 1 to 20 carbon atoms. Preferably, the carbon number is 1 to 10 in view of bulkiness and diffusion distance of the generated acid. In particular, branched or cyclic groups are preferable due to shorter diffusion length. Also, methyl, ethyl, propyl, butyl, octyl groups and the like are preferable due to being inexpensively synthesizable.

The aryl group of the aryl sulfonic acid ions is an aryl group having 6 to 20 carbon atoms, and is exemplified by a phenol group or a naphthyl group that may be unsubstituted or substituted by an alkyl group or a halogen atom. In particular, aryl groups having 6 to 10 carbon atoms are preferred since they can be synthesized inexpensively. Specific examples of the preferable aryl group include phenyl, toluenesulfonyl, ethylphenyl, naphthyl, methylnaphthyl groups and the like.

When hydrogen atoms in the fluoroalkylsulfonic acid ion or the aryl sulfonic acid ion are partially or entirely fluorinated, the fluorination rate is preferably 10% to 100%, and more preferably 50% to 100%; it is particularly preferable that all hydrogen atoms are substituted by fluorine atoms in view of higher acid strength. Specific examples thereof include trifluoromethane sulfonate, perfluorobutane sulfonate, perfluorooctane sulfonate, perfluorobenzene sulfonate, and the like.

Among these, a preferable anion moiety is exemplified by one represented by the following formula (a9).

In the formula (a9), $R^{20a}$ represents a group represented by the following formulae (a10) or (a11), or a group represented by the following formula (a12).

$$—C_xF_{2x+1} \quad (a10)$$

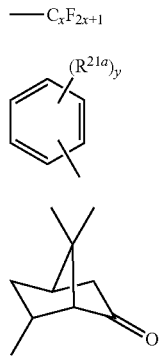

In the formula (a10), x represents an integer of 1 to 4. Also, in the formula (a11), $R^{21a}$ represents a hydrogen atom, a hydroxyl group, a linear or branched alkyl group having 1 to 6 carbon atoms, or a linear or branched alkoxy group having 1 to 6 carbon atoms, and y represents an integer of 1 to 3. Among these, trifluoromethane sulfonate and perfluorobutane sulfonate are preferable in view of safety.

In addition, a nitrogen-containing moiety represented by the following formula (a13) or (a14) may also be used for the anion moiety.

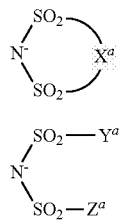

In the formulae (a13) and (a14), $X^a$ represents a linear or branched alkylene group of which at least one hydrogen atom is substituted by a fluorine atom, and the carbon number of the alkylene group is 2 to 6, preferably 3 to 5, and most preferably 3. In addition, each of $Y^a$ and $Z^a$ independently represents a linear or branched alkyl group of which at least one hydrogen atom is substituted by a fluorine atom, the carbon number of the alkyl group is 1 to 10, preferably 1 to 7, and more preferably 1 to 3.

A smaller number of carbon atoms in the alkylene group of $X^a$, or in the alkyl group of $Y^a$ or $Z^a$ is preferred because the solubility in an organic solvent is favorable.

In addition, a larger number of hydrogen atoms substituted by fluorine atoms in the alkylene group of $X^a$, or in the alkyl group of $Y^a$ or $Z^a$ is preferred since the acid strength increases. The percentage of fluorine atoms in the alkylene group or alkyl group, i.e., the fluorination rate, is preferably 70 to 100% and more preferably 90 to 100%, and most preferable are perfluoroalkylene or perfluoroalkyl groups in which all of the hydrogen atoms are substituted by fluorine atoms.

Preferable onium salts having a naphthalene ring at their cation moieties are exemplified by compounds represented by the following formulae (a15) and (a16).

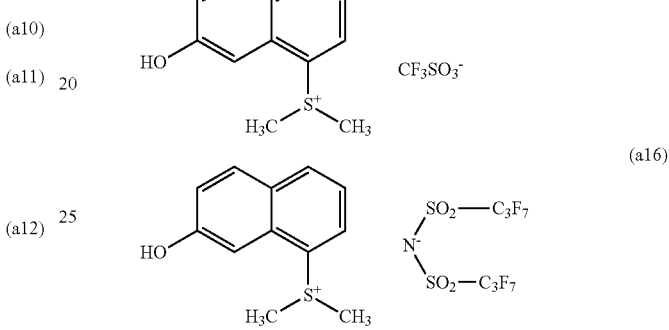

Examples of the fifth aspect of the (A) acid generator include bissulfonyldiazomethanes such as bis(p-toluenesulfonyl)diazomethane, bis(1,1-dimethyl ethylsulfonyl)diazomethane, bis(cyclohexylsulfonyl)diazomethane and bis(2,4-dimethylphenylsulfonyl)diazomethane; nitrobenzyl derivatives such as 2-nitrobenzyl p-toluenesulfonate, 2,6-dinitrobenzyl p-toluenesulfonate, nitrobenzyl tosylate, dinitrobenzyl tosylate, nitrobenzyl sulfonate, nitrobenzyl carbonate and dinitrobenzyl carbonate; sulfonates such as pyrogalloltrimesylate, pyrogalloltritosylate, benzyltosylate, benzylsulfonate, N-methylsulfonyloxysuccinimide, N-trichloromethylsulfonyloxysuccinimide, N-phenylsulfonyloxymaleimide and N-methylsulfonyloxyphthalimide; trifluoromethane sulfonates such as N-hydroxyphthalimide and N-hydroxynaphthalimide; onium salts such as diphenyliodonium hexafluorophosphate, (4-methoxyphenyl)phenyliodonium trifluoromethanesulfonate, bis(p-tert-butylphenyl)iodonium trifluoromethanesulfonate, triphenylsulfonium hexafluorophosphate, (4-methoxyphenyl)diphenylsulfonium trifluoromethanesulfonate and (p-tert-butylphenyl) diphenylsulfonium trifluoromethanesulfonate; benzointosylates such as benzointosylate and α-methylbenzointosylate; other diphenyliodonium salts, triphenylsulfonium salts, phenyldiazonium salts, benzylcarbonates and the like.

The (A) acid generator may be used alone, or in combination of two or more kinds thereof. Furthermore, the content of the (A) acid generator (A) is preferably adjusted to 0.1% to 10% by mass, and more preferably 0.5% to 3% by mass, relative to the total mass of the photosensitive resin composition. When the amount of the acid generator (A) used is adjusted to the range described above, a photosensitive resin composition that is a uniform solution having satisfactory sensitivity and exhibiting excellent storage stability can be readily prepared.

<(B) Resin>

The (B) resin whose alkali solubility increases under the action of an acid is not particularly limited, and an arbitrary resin whose alkali solubility increases under the action of an acid can be used. Among these, at least one resin selected from the group consisting of (B1) novolak resin, (B2) polyhydroxystyrene resin and (B3) acrylic resin is preferably contained.

[(B1) Novolak Resin]

As the (B1) novolak resin, a resin including the structural unit represented by the following formula (b1) can be used.

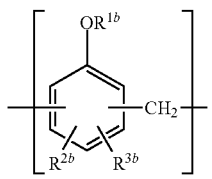

(b1)

In the formula (b1), $R^{1b}$ represents an acid-dissociative dissolution-controlling group, and each of $R^{2b}$ and $R^{3b}$ independently represents a hydrogen atom or an alkyl group having 1 to 6 carbon atoms.

The acid-dissociative dissolution-controlling group represented by the above $R^{1b}$ is preferably a group represented by the following formula (b2) or (b3), a linear, branched or cyclic alkyl group having 1 to 6 carbon atoms, a vinyloxyethyl group, a tetrahydropyranyl group, a tetrafuranyl group, or a trialkylsilyl group.

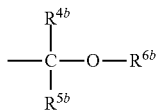

(b2)

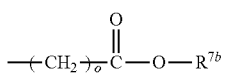

(b3)

In the formulae (b2) and (b3), each of $R^{4b}$ and $R^{5b}$ independently represents a hydrogen atom, or a linear or branched alkyl group having 1 to 6 carbon atoms, $R^{6b}$ represents a linear, branched or cyclic alkyl group having 1 to 10 carbon atoms, $R^{7b}$ represents a linear, branched or cyclic alkyl group having 1 to 6 carbon atoms, and o represents 0 or 1.

Examples of the linear or branched alkyl group include a methyl group, an ethyl group, a propyl group, an isopropyl group, an n-butyl group, an isobutyl group, a tert-butyl group, a pentyl group, an isopentyl group, a neopentyl group, and the like. Further, examples of the cyclic alkyl group include a cyclopentyl group, a cyclohexyl group, and the like.

Specific examples of the acid-dissociative dissolution-controlling group represented by the formula (b2) include a methoxyethyl group, ethoxyethyl group, n-propoxyethyl group, isopropoxyethyl group, n-butoxyethyl group, isobutoxyethyl group, tert-butoxyethyl group, cyclohexyloxyethyl group, methoxypropyl group, ethoxypropyl group, 1-methoxy-1-methylethyl group, 1-ethoxy-1-methylethyl group, and the like. Furthermore, specific examples of the acid-dissociative dissolution-controlling group represented by the formula (b3) include a tert-butoxycarbonyl group, tert-butoxycarbonylmethyl group, and the like. Examples of the trialkylsilyl group include a trimethylsilyl group and tri-tert-butyldimethylsilyl group in which each alkyl group has 1 to 6 carbon atoms.

[(B2) Polyhydroxystyrene Resin]

As the (B2) polyhydroxystyrene resin, a resin including the structural unit represented by the following formula (b4) can be used.

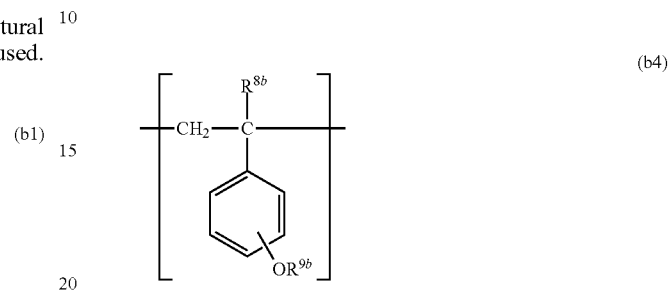

(b4)

In the formula (b4), $R^{8b}$ represents a hydrogen atom or an alkyl group having 1 to 6 carbon atoms, and $R^{9b}$ represents an acid-dissociative dissolution-controlling group.

The alkyl group having 1 to 6 carbon atoms is, for example, a linear, branched or cyclic alkyl group having 1 to 6 carbon atoms. Examples of the linear or branched alkyl group include a methyl group, ethyl group, propyl group, isopropyl group, n-butyl group, isobutyl group, tert-butyl group, pentyl group, isopentyl group and neopentyl group, and examples of the cyclic alkyl group include a cyclopentyl group and cyclohexyl group.

The acid-dissociative dissolution-controlling group represented by the $R^{9b}$ can be acid-dissociative dissolution-controlling groups similar to those exemplified in the above formulae (b2) and (b3).

Furthermore, the (B2) polyhydroxystyrene resin can include another polymerizable compound as a structural unit in order to moderately control physical or chemical properties. The polymerizable compound is exemplified by conventional radical polymerizable compounds and anion polymerizable compounds. Examples of the polymerizable compound include monocarboxylic acids such as acrylic acid, methacrylic acid and crotonic acid; dicarboxylic acids such as maleic acid, fumaric acid and itaconic acid; methacrylic acid derivatives having a carboxy group and an ester bond such as 2-methacryloyloxyethyl succinic acid, 2-methacryloyloxyethyl maleic acid, 2-methacryloyloxyethyl phthalic acid and 2-methacryloyloxyethyl hexahydrophthalic acid; (meth)acrylic acid alkyl esters such as methyl(meth)acrylate, ethyl (meth)acrylate and butyl (meth)acrylate; (meth)acrylic acid hydroxyalkyl esters such as 2-hydroxyethyl (meth)acrylate and 2-hydroxypropyl (meth)acrylate; (meth)acrylic acid aryl esters such as phenyl (meth)acrylate and benzyl (meth)acrylate; dicarboxylic acid diesters such as diethyl maleate and dibutyl fumarate; vinyl group-containing aromatic compounds such as styrene, α-methylstyrene, chlorostyrene, chloromethylstyrene, vinyltoluene, hydroxystyrene, α-methylhydroxystyrene and α-ethylhydroxystyrene; vinyl group-containing aliphatic compounds such as vinyl acetate; conjugated diolefins such as butadiene and isoprene; nitrile group-containing polymerizable compounds such as acrylonitrile and methacrylonitrile; chlorine-containing polymerizable compounds such as vinyl chloride and vinylidene chloride; and amide bond-containing polymerizable compounds such as acrylamide and methacrylamide.

[(B3) Acrylic Resin]

As the (B3) acrylic resin, a resin including structural units represented by the following formulae (b5) to (b7) can be used.

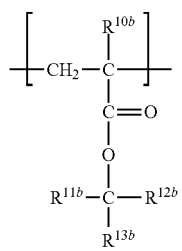
(b5)

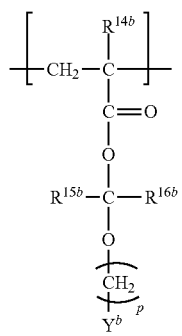
(b6)

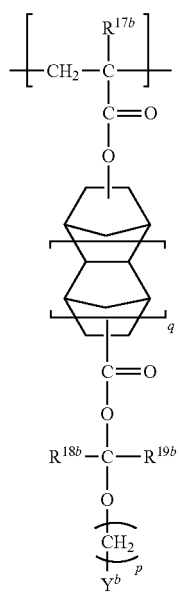
(b7)

Each of $R^{10b}$ and $R^{14b}$ to $R^{19b}$ in the above formulae (b5) to (b7) is independently a hydrogen atom, a linear or branched alkyl group having 1 to 6 carbon atoms, a fluorine atom or a linear or branched fluorinated alkyl group having 1 to 6 carbon atoms; each of $R^{11b}$ to $R^{13b}$ is independently a linear or branched alkyl group having 1 to 6 carbon atoms or a linear or branched fluorinated alkyl group having 1 to 6 carbon atoms; $R^{12b}$ and $R^{13b}$ may be bonded to each other to form a hydrocarbon ring having 5 to 20 carbon atoms along with a carbon atom to which both are attached; $Y^b$ represents an aliphatic cyclic group or an alkyl group optionally having a substituent; p is an integer of 0 to 4; and q is 0 or 1.

Examples of the linear or branched alkyl group include a methyl group, ethyl group, propyl group, isopropyl group, n-butyl group, isobutyl group, tert-butyl group, pentyl group, isopentyl group, neopentyl group, and the like. The fluorinated alkyl group refers to the abovementioned alkyl groups of which the hydrogen atoms are partially or entirely substituted by fluorine atoms.

In the case of the $R^{12b}$ and $R^{13b}$ not being bonded to each other to form a hydrocarbon ring, a linear or branched alkyl group having 2 to 4 carbon atoms is preferred as the $R^{11b}$, $R^{12b}$ and $R^{13b}$ in view of high contrast, superior resolution, superior focal depth-width and the like. As the above $R^{15b}$, $R^{16b}$, $R^{18b}$ and $R^{19b}$, preferred is a hydrogen atom or a methyl group.

The above $R^{12b}$ and $R^{13b}$ may form an aliphatic cyclic group having 5 to 20 carbon atoms along with a carbon atom to which both are attached. Specific examples of such an aliphatic cyclic group include a group in which one or more hydrogen atoms are removed from monocycloalkane; and polycycloalkane such as bicycloalkane, tricycloalkane and tetracycloalkane. Specifically, they include a group in which one or more hydrogen atoms are removed from monocycloalkane such as cyclopentane, cyclohexane, cycloheptane, and cyclooctane; and polycycloalkane such as adamantane, norbornane, isobornane, tricyclodecane and tetracyclododecane; and the like. In particular, preferred is a group (optionally further having a substituent) in which one or more hydrogen atoms are removed from cyclohexane and adamantane.

Further, in a case where an aliphatic cyclic group to be formed with the above $R^{12b}$ and $R^{13b}$ has a substituent on the ring backbone thereof, examples of the above substituent include a polar group such as a hydroxy group, a carboxy group, a cyano group and an oxygen atom (=O), and a linear or branched alkyl group having 1 to 4 carbon atoms. As the polar group, an oxygen atom (=O) is particularly preferred.

The aforementioned $Y^b$ is an aliphatic cyclic group or an alkyl group; and examples thereof are monocycloalkanes and polycycloalkanes such as bicycloalkanes, tricycloalkanes and tetracycloalkanes from which at least one hydrogen atom is removed. Specific examples thereof are monocycloalkanes such as cyclopentane, cyclohexane, cycloheptane and cyclooctane, and polycycloalkanes such as adamantane, norbornane, isobornane, tricyclodecane and tetracyclododecane, from which at least one hydrogen atom is removed. Particularly preferable is adamantane from which at least one hydrogen atom is removed (that may further have a substituent).

When the aliphatic cyclic group of the abovementioned $Y^b$ has a substituent on the ring backbone thereof, the substituent is exemplified by polar groups such as a hydroxide group, carboxy group, cyano group and oxygen atom (=O), and linear or branched alkyl groups having 1 to 4 carbon atoms. The polar group is preferably an oxygen atom (=O) in particular.

When $Y^b$ is an alkyl group, it is preferably a linear or branched alkyl group having 1 to 20 carbon atoms, and more preferably 6 to 15 carbon atoms. Preferably, the alkyl group is an alkoxyalkyl group in particular; and examples of the alkoxyalkyl group include a 1-methoxyethyl group, 1-ethoxyethyl group, 1-n-propoxyethyl group, 1-isopropoxyethyl group, 1-n-butoxyethyl group, 1-isobutoxyethyl group, 1-tert-butoxyethyl group, 1-methoxypropyl group, 1-ethoxypropyl group, 1-methoxy-1-methylethyl group, 1-ethoxy-1-methylethyl group, and the like.

Specific preferred examples of the structural unit represented by the above formula (b5) are those represented by the following formulae (b5-1) to (b5-33).
(b5-1)
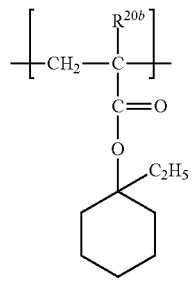
(b5-2)
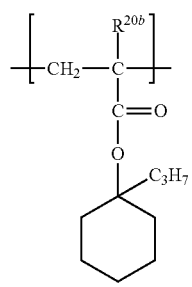
(b5-3)
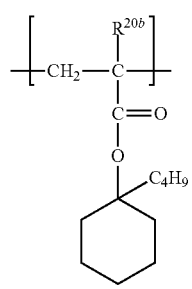
(b5-4)
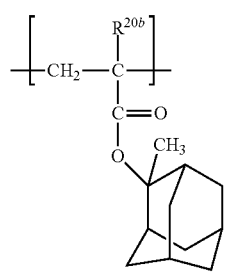
(b5-5)
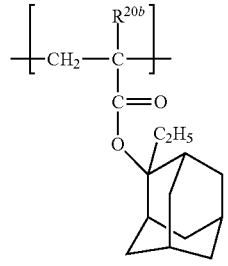
-continued
(b5-6)
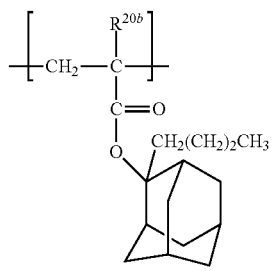
(b5-7)
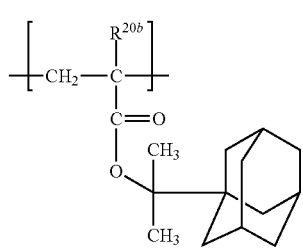
(b5-8)
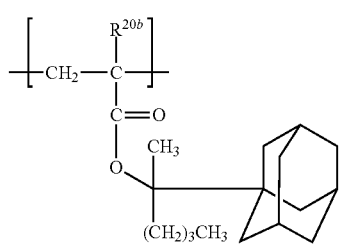
(b5-9)
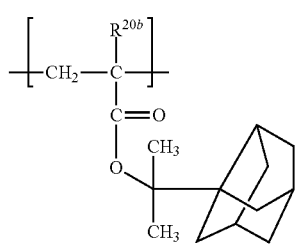
(b5-10)
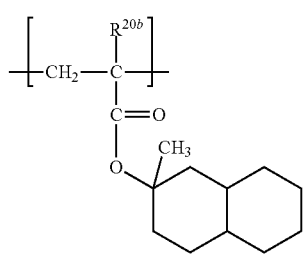
(b5-11)
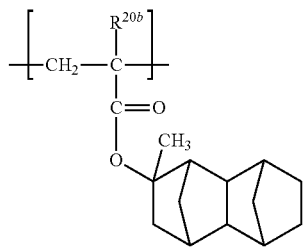

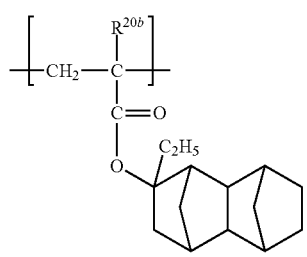
(b5-12)
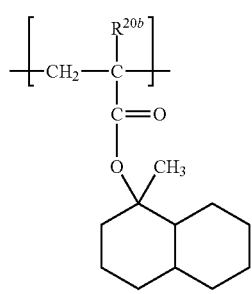
(b5-13)
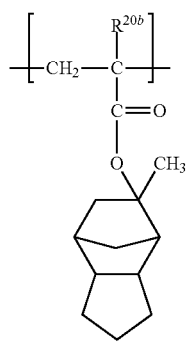
(b5-14)
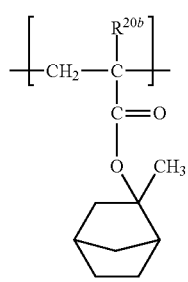
(b5-15)
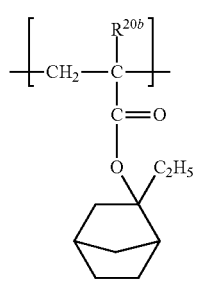
(b5-16)
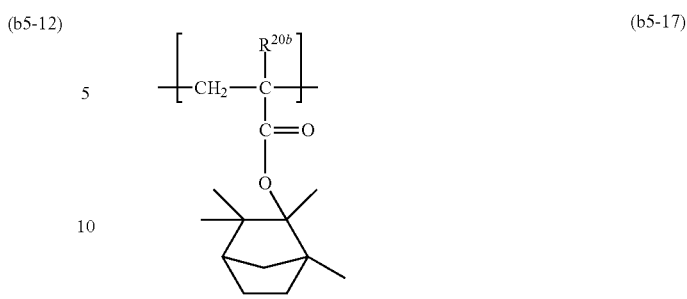
(b5-17)
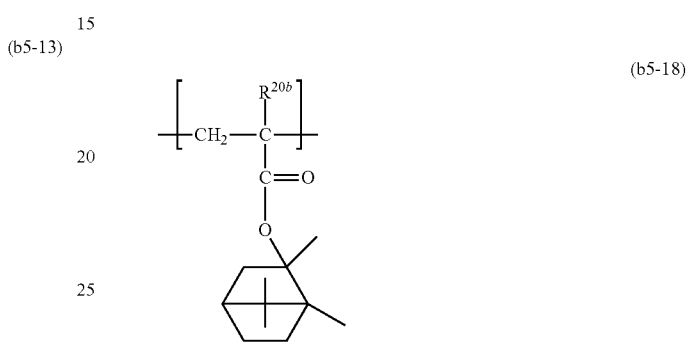
(b5-18)
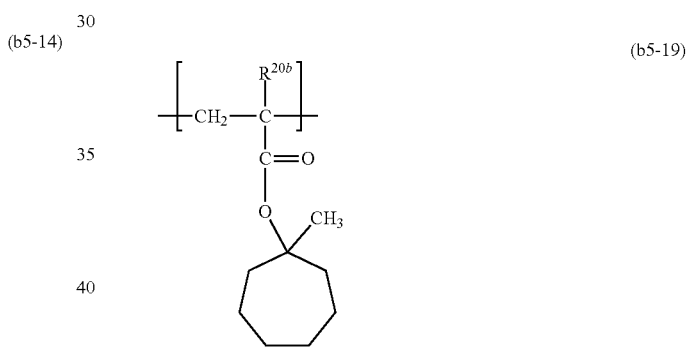
(b5-19)
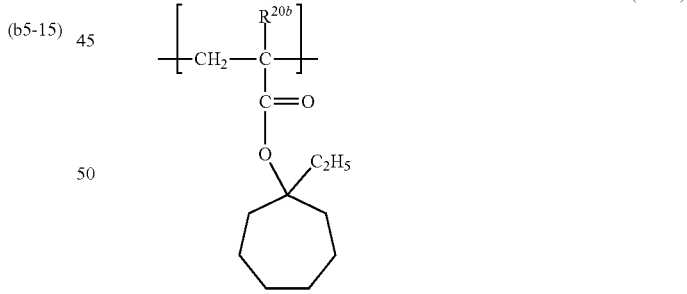
(b5-20)
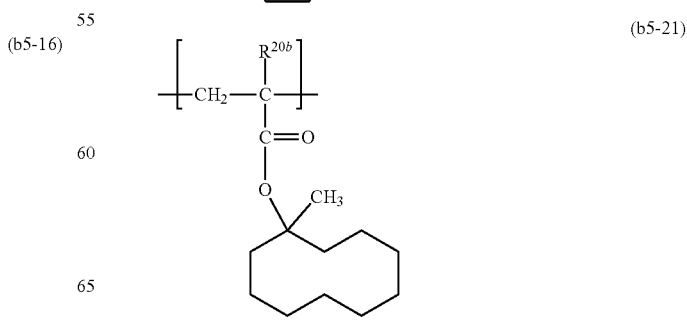
(b5-21)

(b5-22) 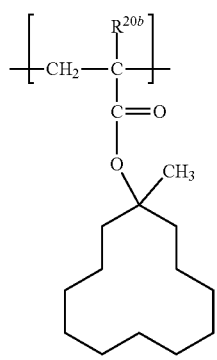
(b5-23) 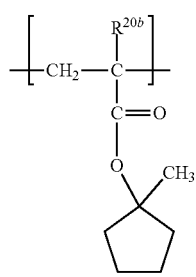
(b5-24) 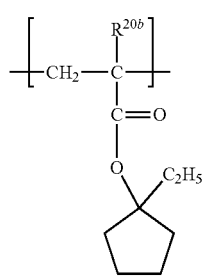
(b5-25) 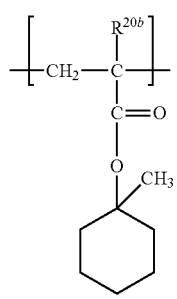
(b5-26) 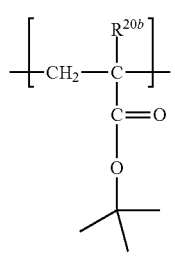
(b5-27) 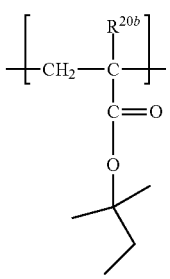
(b5-28) 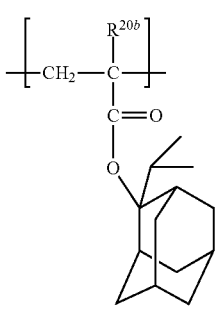
(b5-29) 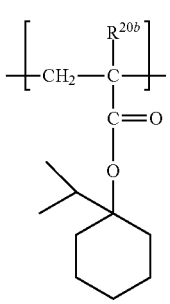
(b5-30) 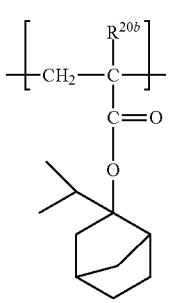
(b5-31) 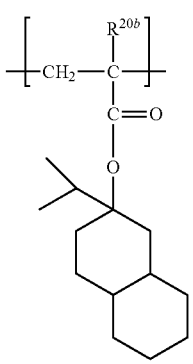

(b5-32)
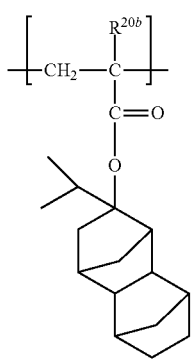
(b5-33)
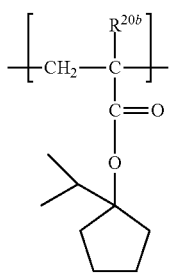
In the above formulae (b5-1) to (b5-33), $R^{20b}$ represents a hydrogen atom or a methyl group.
Specific preferred examples of the structural unit represented by the above formula (b6) include those represented by the following formulae (b6-1) to (b6-24).
(b6-1)
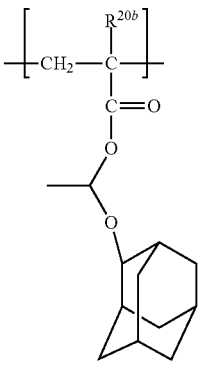
(b6-2)
(b6-3)
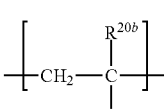
(b6-4)
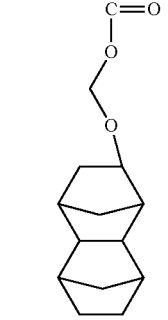
(b6-5)
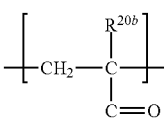
(b6-6)
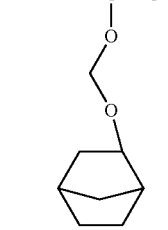

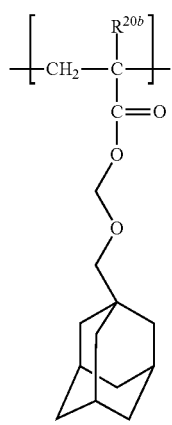
(b6-7)
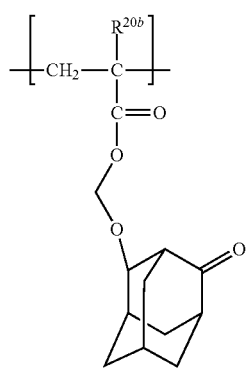
(b6-8)
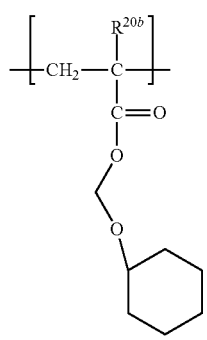
(b6-9)
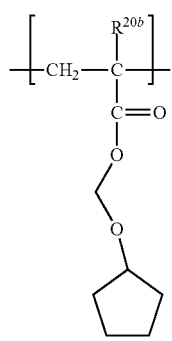
(b6-10)
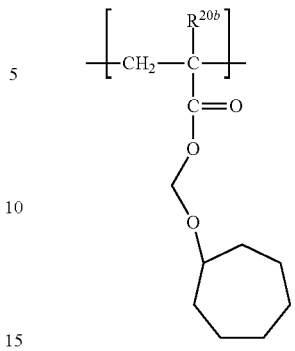
(b6-11)
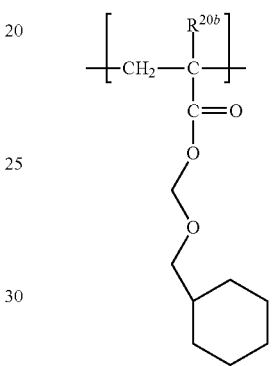
(b6-12)
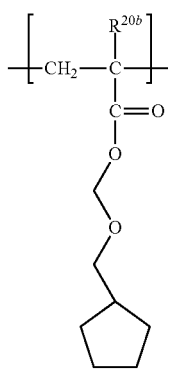
(b6-13)
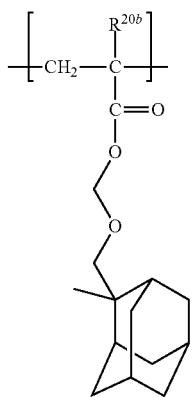
(b6-14)

-continued
(b6-15)
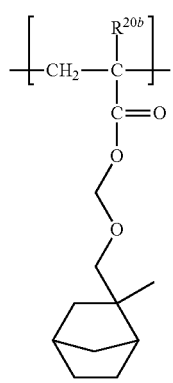
(b6-16)
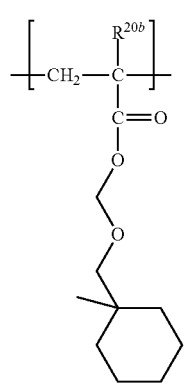
(b6-17)
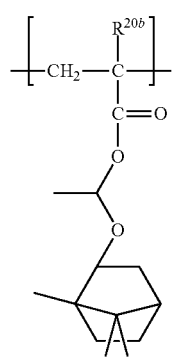
(b6-18)
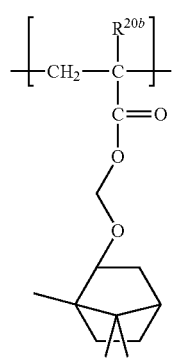
(b6-19)
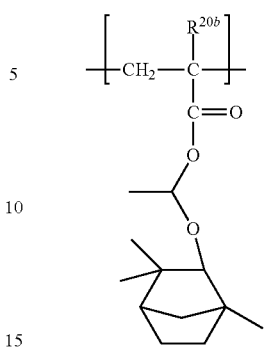
(b6-20)
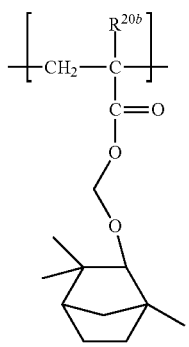
(b6-21)
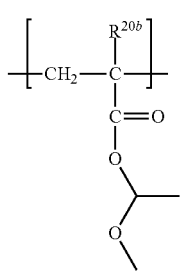
(b6-22)
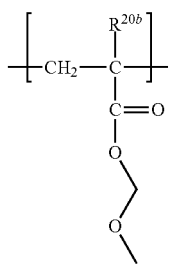
(b6-23)
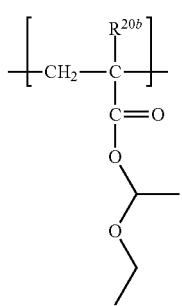

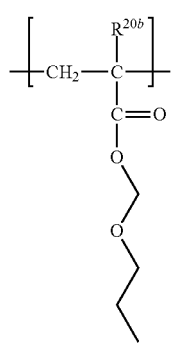
(b6-24)
In the above formulae (b6-1) to (b6-24), $R^{20b}$ represents a hydrogen atom or a methyl group.
Specific preferred examples of the structural unit represented by the above formula (b7) include those represented by the following formulae (b7-1) to (b7-15).
(b7-1)
(b7-2)
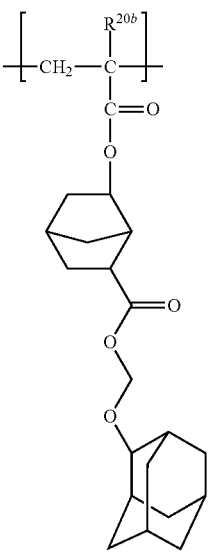
(b7-3)
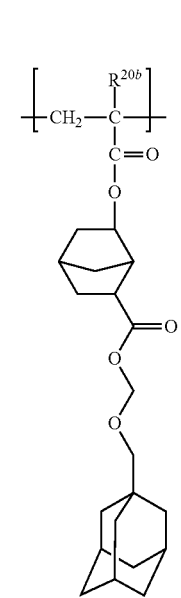
(b7-4)
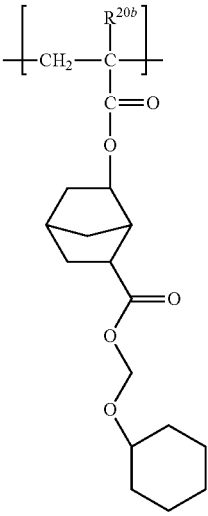
(b7-5)

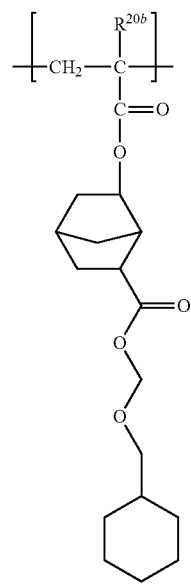
(b7-6)
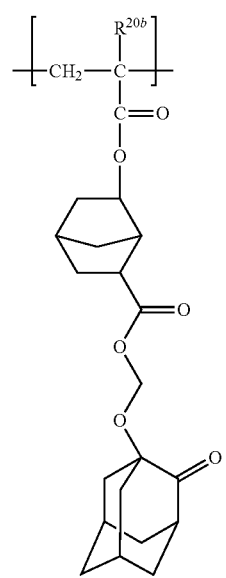
(b7-7)
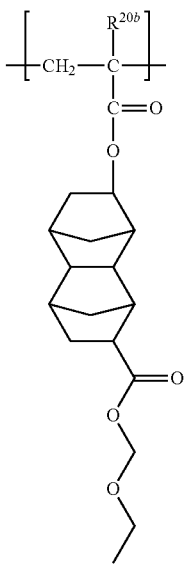
(b7-8)
(b7-9)
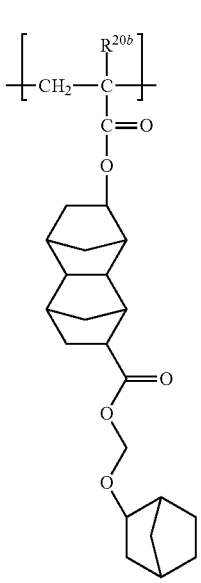
(b7-10)

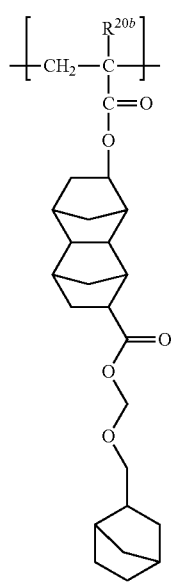 (b7-11)
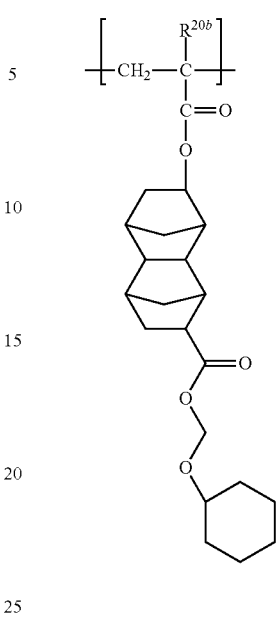 (b7-13)
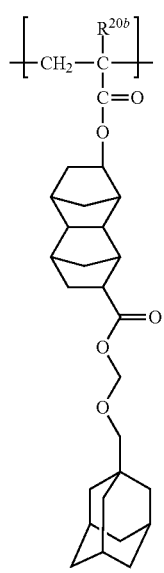 (b7-12)
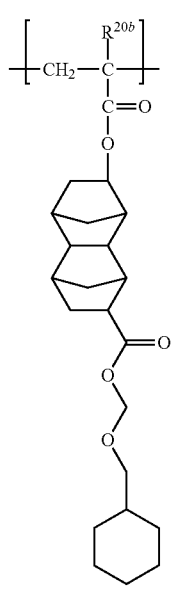 (b7-14)

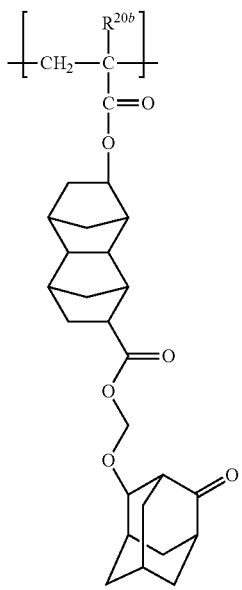

(b7-15)

In the above formulae (b7-1) to (b7-15), $R^{20b}$ represents a hydrogen atom or a methyl group.

It is also preferred that the (B3) acrylic resin consists of a copolymer containing a structural unit derived from a polymerizable compound having an ether bond in addition to the structural unit represented by the above formulae (b5) to (b7).

Illustrative examples of the polymerizable compound having an ether bond include radical polymerizable compounds such as (meth)acrylic acid derivatives having an ether bond and an ester bond, and specific examples thereof include 2-methoxyethyl (meth)acrylate, 2-ethoxyethyl (meth)acrylate, methoxytriethylene glycol (meth)acrylate, 3-methoxybutyl (meth)acrylate, ethylcarbitol (meth)acrylate, phenoxypolyethylene glycol (meth)acrylate, methoxypolyethylene glycol (meth)acrylate, methoxypolypropylene glycol (meth)acrylate, tetrahydrofurfuryl (meth)acrylate, and the like. Also, the polymerizable compound having an ether bond is preferably 2-methoxyethyl (meth)acrylate, 2-ethoxyethyl (meth)acrylate, or methoxytriethylene glycol (meth)acrylate. These polymerizable compounds may be used alone, or in combination of two or more kinds thereof.

Furthermore, the (B3) acrylic resin may contain another polymerizable compound as a structural unit in order to moderately control physical or chemical properties. The polymerizable compound is exemplified by conventional radical polymerizable compounds and anion polymerizable compounds.

Examples of the polymerizable compound include monocarboxylic acids such as acrylic acid, methacrylic acid and crotonic acid; dicarboxylic acids such as maleic acid, fumaric acid and itaconic acid; methacrylic acid derivatives having a carboxy group and an ester bond such as 2-methacryloyloxyethyl succinic acid, 2-methacryloyloxyethyl maleic acid, 2-methacryloyloxyethyl phthalic acid and 2-methacryloyloxyethyl hexahydrophthalic acid; (meth) acrylic acid alkyl esters such as methyl(meth)acrylate, ethyl (meth)acrylate, butyl(meth)acrylate and cyclohexyl(meth) acrylate; (meth)acrylic acid hydroxyalkyl esters such as 2-hydroxyethyl (meth)acrylate and 2-hydroxypropyl (meth) acrylate; (meth)acrylic acid aryl esters such as phenyl (meth) acrylate and benzyl (meth)acrylate; dicarboxylic acid diesters such as diethyl maleate and dibutyl fumarate; vinyl group-containing aromatic compounds such as styrene, α-methylstyrene, chlorostyrene, chloromethylstyrene, vinyltoluene, hydroxystyrene, α-methylhydroxystyrene and α-ethylhydroxystyrene; vinyl group-containing aliphatic compounds such as vinyl acetate; conjugated diolefins such as butadiene and isoprene; nitrile group-containing polymerizable compounds such as acrylonitrile and methacrylonitrile; chlorine-containing polymerizable compounds such as vinyl chloride and vinylidene chloride; amide bond-containing polymerizable compounds such as acrylamide and methacrylamide; and the like.

Furthermore, examples of the polymerizable compound include (meth)acrylic acid esters having a non-acid-dissociative aliphatic polycyclic group, and vinyl group-containing aromatic compounds. As the non-acid-dissociative aliphatic polycyclic group, particularly, a tricyclodecanyl group, an adamantyl group, a tetracyclododecanyl group, an isobornyl group, a norbornyl group, and the like are preferred from the viewpoint of easy industrial availability. These aliphatic polycyclic groups may have a linear or branched alkyl group having 1 to 5 carbon atoms as a substituent.

Specific examples of the (meth)acrylic acid esters having a non-acid-dissociative aliphatic polycyclic group include compounds having structures represented by the following formulae (b8-1) to (b8-5).

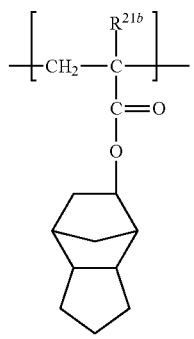

(b8-1)

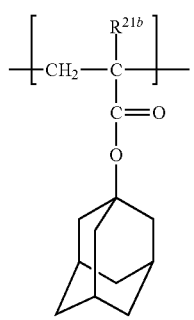

(b8-2)

-continued (b8-3)

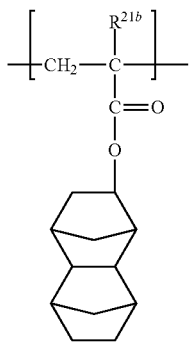

(b8-4)

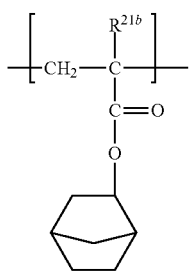

(b8-5)

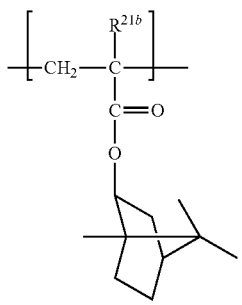

In formulae (b8-1) to (b8-5) $R^{21b}$ represents a hydrogen atom or a methyl group.

Among the (B) resins, the (B3) acrylic resins are preferably used. Among such (B3) acrylic resins, a copolymer having a constituent unit represented by formula (b5), a constituent unit derived from (meth)acrylic acid, a constituent unit derived from a (meth)acrylic acid alkyl ester, and a constituent unit derived from a (meth)acrylic acid aryl ester is preferred.

Such a copolymer is preferably a copolymer represented by the following formula (b9).

(b9)

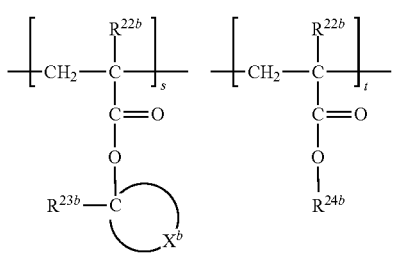

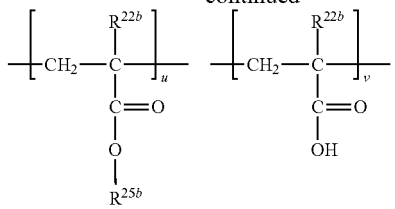

In the formula (b9), $R^{22b}$ represents a hydrogen atom or a methyl group; $R^{23b}$ represents a linear or a branched alkyl group having 2 to 4 carbon atoms; $X^b$ represents a hydrocarbon ring having 5 to 20 carbon atoms formed along with a carbon atom to which it is attached; $R^{24b}$ a linear or branched alkyl group having 1 to 6 carbon atoms or an alkoxyalkyl group having 1 to 6 carbon atoms; and $R^{25b}$ represents an aryl group having 6 to 12 carbon atoms.

In regard to the copolymers represented by the above formula (b9), s, t, u and v represent molar ratios of respective structural units, with s being 8 to 45% by mole, t being 10 to 65% by mole, u being 3 to 25% by mole, and v being 6 to 25% by mole.

The polystyrene equivalent mass average molecular weight of the (B) resin is preferably 10,000 to 600,000, more preferably 20,000 to 400,000, and still more preferably 30,000 to 300,000. By thus adjusting the mass average molecular weight, the photosensitive resin layer can maintain sufficient strength without deteriorating peel properties with the surface of the substrate, and also swelling of profiles in plating, and generation of cracks can be prevented.

It is also preferred that the resin (B) has a dispersivity of no less than 1.05. As used herein, dispersivity indicates a value of a mass average molecular weight divided by a number average molecular weight. The dispersivity in the range described above can avoid problems with respect to stress resistance on intended plating or possible swelling of metal layers resulting from the plating process.

The content of the (B) resin is preferably 5 to 60% by mass with respect to the total mass of the photosensitive rein composition according to the present invention.

<(C) Fluorene Compound>

The (C)fluorene compound is represented by the following formula (1).

(1)

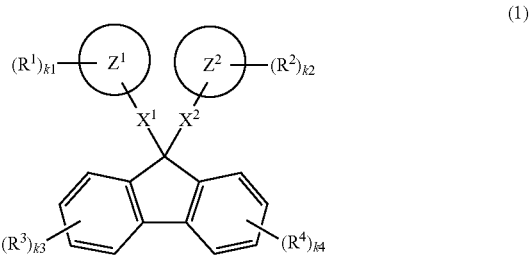

wherein each of ring $Z^1$ and ring $Z^2$ independently represents a benzene ring or a naphthalene ring; each of $X^1$ and $X^2$ independently represents a single bond or —S—; each of $R^1$, $R^2$, $R^3$, and $R^4$ independently represents a monovalent hydrocarbon group, a hydroxyl group, a (meth)acryloyloxy group, a group represented by —$OR^{4a}$, a group represented by —$SR^{4b}$, an acyl group, an alkoxycarbonyl group, a halogen atom, a nitro group, a cyano group, a mercapto group, a carboxy group, an amino group, a carbamoyl group, a group represented by —NHR$^{4c}$, a group represented by —N(R$^{4d}$)$_2$, a (meth)acryloyloxy group, a sulfo group, or a group in which at least a part of the hydrogen atoms bonded to a carbon atom contained in a monovalent hydrocarbon group, a group represented by —OR$^{4a}$, a group represented by —SR$^{4b}$, an acyl group, an alkoxycarbonyl group, a group represented by —NHR$^{4c}$, or a group represented by —N(R$^{4d}$)$_2$ is substituted by a monovalent hydrocarbon group, a hydroxyl group, a group represented by —OR$^{4a}$, a group represented by —SR$^{4b}$, an acyl group, an alkoxycarbonyl group, a halogen atom, a nitro group, a cyano group, a mercapto group, a carboxy group, an amino group, a carbamoyl group, a group represented by —NHR$^{4c}$, a group represented by —N(R$^{4d}$)$_2$, a (meth)acryloyloxy group, a mesyloxy group, or a sulfo group; each of R$^{4a}$ to R$^{4d}$ independently represents a monovalent hydrocarbon group; and each of k1, k2, k3, and k4 independently represents an integer of 0 to 4.

Each of ring Z$^1$ and ring Z$^2$ independently represents a benzene ring or a naphthalene ring, and, more preferably, both the ring Z$^1$ and the ring Z$^2$ are benzene rings or naphthalene rings.

In the general formula (1), each of X$^1$ and X$^2$ independently represents a single bond or a group represented by —S—, typically a single bond.

In the general formula (1), examples of R$^1$, R$^2$, R$^3$, and R$^4$ include, for example, a monovalent hydrocarbon group such as an alkyl group, for example, a C$_{1-12}$ alkyl group such as a methyl group, an ethyl group, a propyl group, an isopropyl group, or a butyl group, preferably a C$_{1-8}$ alkyl group, more preferably C$_{1-6}$alkyl group or the like, a cycloalkyl group, for example, a C$_{5-10}$ cycloalkyl group such as a cyclohexyl group, preferably a C$_{5-8}$ cycloalkyl group, more preferably a C$_{5-6}$ cycloalkyl group or the like, an aryl group, for example, a C$_{6-14}$aryl group such as a phenyl group, a tolyl group, a xylyl group, or a naphthyl group, preferably a C$_{6-10}$aryl group, more preferably a C$_{6-8}$ aryl group or the like, or an aralkyl group, for example, a C$_{6-10}$ aryl-C$_{1-4}$ alkyl group such as a benzyl group or a phenethyl group; a hydroxyl group; or a group represented by —OR$^{4a}$ wherein R$^{4a}$ represents a monovalent hydrocarbon group, for example, the above-exemplified monovalent hydrocarbon group, for example, an alkoxy group, for example, a C$_{1-12}$ alkoxy group such as a methoxy group, an ethoxy group, a propoxy group, or a butoxy group, preferably a C$_{1-8}$ alkoxy group, more preferably a C$_{1-6}$ alkoxy group, a cycloalkoxy group, for example, a C$_{5-10}$ cycloalkoxy group, an aryloxy group, for example, a C$_{6-10}$ aryloxy group such as a phenoxy group, an aralkyloxy group, for example, a C$_{6-10}$ aryl-C$_{1-4}$ alkyloxy group such as a benzyloxy group; a group represented by —SR$^{4b}$ wherein R$^{4b}$ represents a monovalent hydrocarbon group, for example, the above-exemplified monovalent hydrocarbon group, for example, an alkylthio group, for example, a C$_{1-12}$ alkylthio group such as a methylthio group, an ethylthio group, a propylthio group, a butylthio group, preferably a C$_{1-8}$ alkylthio group, more preferably a C$_{1-6}$ alkylthio group, a cycloalkylthio group, for example, a C$_{5-10}$ cycloalkylthio group such as a cyclohexylthio group, an arylthio group, for example, a C$_{6-10}$ arylthio group such as a phenylthio group, an aralkylthio group, for example, a C$_{6-10}$ aryl-C$_{1-4}$ alkylthio group such as a benzylthio group; an acyl group, for example, a C$_{1-6}$ acyl group such as an acetyl group; an alkoxycarbonyl group, for example, a C$_{1-4}$ alkoxycarbonyl group such as a C$_{1-4}$ alkoxycarbonyl group such as a methoxycarbonyl group; a halogen atom, for example, a fluorine atom, a chlorine atom, a bromine atom, or an iodine atom; a nitro group; a cyano or mercapto group; a carboxyl, amino, or carbamoyl group; or a group represented by —NHR$^{4c}$ wherein R$^{4c}$ represents a monovalent hydrocarbon group, for example, the above-exemplified monovalent hydrocarbon group, for example, an alkylamino group, for example, a C$_{1-12}$ alkylamino group such as a methylamino group, an ethylamino group, a propylamino group, or a butylamino group, preferably a C$_{1-8}$ alkylamino group, more preferably a C$_{1-6}$ alkylamino group, a cycloalkylamino group, for example, a C$_{5-10}$ cycloalkylamino group such as a cyclohexylamino group, an arylamino group, for example, a C$_{6-10}$ arylamino group such as a phenylamino group, or an aralkylamino group, for example, a C$_{6-10}$ aryl-C$_{1-4}$ alkylamino group such as a benzylamino group; a group represented by —N(R$^{4d}$)$_2$ wherein each R$^{4d}$ independently represents a monovalent hydrocarbon group, for example, the above-exemplified monovalent hydrocarbon group, for example, a dialkylamino group, for example, a di(C$_{1-12}$ alkyl) amino group such as a dimethylamino group, a diethylamino group, a dipropylamino group, or a dibutylamino group, preferably a (C$_{1-8}$ alkyl)amino group, more preferably a di(C$_{1-6}$ alkyl) amino group, a dicycloalkylamino group, for example, a di(C$_{5-10}$ cycloalkyl)amino group such as a dicyclohexylamino group, a diarylamino group, for example, a di(C$_{6-10}$ aryl)amino group such as a diphenylamino group, a diaralkylamino group, for example, a di(C$_{6-10}$ aryl-C$_{1-4}$ alkyl) amino group such as a dibenzylamino group; a (meth) acryloyloxy group; a sulfo group; or the above monovalent hydrocarbon group, a group represented by —OR$^{4a}$, a group represented by —SR$^{4b}$, an acyl group, an alkoxycarbonyl group, a group represented by —NHR$^{4c}$, or a group represented by —N(R$^{4d}$)$_2$, in which at least a part of hydrogen atoms bonded to a carbon atom contained in these groups is substituted by the above monovalent hydrocarbon group, a hydroxyl group, a group represented by —OR$^{4a}$, a group represented by —SR$^{4b}$, an acyl group, an alkoxycarbonyl group, a halogen atom, a nitro group, a cyano group, a mercapto group, a carboxy group, an amino group, a carbamoyl group, a group represented by —NHR$^{4c}$, a group represented by —N(R$^{4d}$)$_2$, a (meth)acryloyloxy group, a mesyloxy group, or a sulfo group, for example, an alkoxyaryl group, for example, a C$_{1-4}$ alkoxy C$_{6-10}$aryl group such as a methoxyphenyl group, an alkoxycarbonylaryl group, for example, a C$_{1-4}$ alkoxycarbonyl C$_{6-10}$aryl group such as a methoxycarbonylphenyl group, or an ethoxycarbonylphenyl group.

Among them, typical examples thereof include groups in which R$^1$, R$^2$, R$^3$, and R$^4$ represent a hydroxyl group, a hydroxyalkyl group having 1 to 4 carbon atoms, a (meth) acryloyloxy group, a monovalent hydrocarbon group, a group represented by —OR$^{4a}$, a group represented by —SR$^{4b}$, an acyl group, an alkoxycarbonyl group, a halogen atom, a nitro group, a cyano group, a group represented by —NHR$^{4c}$, or a group represented by —N(R$^{4d}$)$_2$.

R$^1$ and R$^2$ preferably represent a hydroxyl group, a hydroxyalkyl group having 1 to 4 carbon atoms or a (meth) acryloyloxy group, particularly preferably represent a hydroxyl group or a (meth)acryloyloxy group.

Preferred examples of R$^3$ and R$^4$ include monovalent hydrocarbon groups, for example, alkyl groups, for example, C$_{1-6}$alkyl groups, cycloalkyl groups, for example, C$_{5-8}$ cycloalkyl groups, aryl groups, for example, C$_{6-10}$ aryl groups, aralkyl groups, for example, C$_{6-8}$ aryl-C$_{1-2}$ alkyl groups, and alkoxy groups, for example, C$_{1-4}$ alkoxy groups. In particular, R$^{2a}$ and R$^{2b}$ preferably represent a monovalent hydrocarbon group such as an alkyl group, for example, a $C_{1-4}$ alkyl group, particularly a methyl group, an aryl group, for example, a $C_{6-10}$ aryl group, particularly a phenyl group, particularly preferably represent an alkyl group.

Note that when the total of k1, k2, k3, and k4 is an integer of 2 or more, the corresponding $R^1$, $R^2$, $R^3$, and $R^4$ may be respectively identical to or different from each other. For example, $R^1$ contained in ring $Z^1$ and $R^2$ contained in ring $Z^2$ may be identical to or different from each other. Further, $R^3$ and $R^4$ may be identical to or different from each other. The position of a substituent in ring $Z^1$ in $R^1$, the position of a substituent in ring $Z^2$ in $R^2$, and the position of a substituent in the benzo ring in $R^3$, and the position of a substituent in the benzo ring in $R^4$ are not particularly limited.

In the general formula (1), k1, k2, k3, and k4 may be selected depending upon the type of ring $Z^1$ and ring $Z^2$ and, for example, may be an integer of 0 to 4, preferably an integer of 0 to 3, more preferably an integer of 0 to 2.

k1, k2, k3, and k4 may be independent of each other and may be identical to or different from each other. The content of the (C) fluorene compound is preferably 1 to 50% by mass, more preferably 5 to 40% by mass, particularly preferably 10 to 30% by mass, relative to the total mass of the photosensitive resin composition.

In the present embodiment, when the (C) fluorene compound is contained, a pattern having a wide DOF margin and a high level of rectangular profile can be formed, although the mechanism of action has not been elucidated yet.

<(D) Alkali-Soluble Resin>

It is preferred that the photosensitive resin composition further contains a (D) alkali-soluble resin in order to improve crack resistance. The alkali-soluble resin as referred to herein may be determined as follows. A solution of the resin to give a resin concentration of 20% by mass (solvent:propylene glycol monomethyl ether acetate) is used to form a resin film having a film thickness of 1 μm on a substrate, and immersed in an aqueous 2.38% by mass TMAH solution for 1 min. If the resin was dissolved in an amount of no less than 0.01 μm, the resin is defined to be alkali soluble. The (D) alkali-soluble resin is preferably at least one selected from the group consisting of (D1) novolak resin, (D2) polyhydroxystyrene resin and (D3) acrylic resin.

[(D1) Novolak Resin]

The (D1) novolak resin may be prepared by addition condensation between, for example, aromatic compounds having a phenolic hydroxy group (hereinafter, merely referred to as "phenols") and aldehydes in the presence of an acid catalyst.

Examples of the phenols include phenol, o-cresol, m-cresol, p-cresol, o-ethylphenol, m-ethylphenol, p-ethylphenol, o-butylphenol, m-butylphenol, p-butylphenol, 2,3-xylenol, 2,4-xylenol, 2,5-xylenol, 2,6-xylenol, 3,4-xylenol, 3,5-xylenol, 2,3,5-trimethyl phenol, 3,4,5-trimethyl phenol, p-phenylphenol, resorcinol, hydroquinone, hydroquinone monomethyl ether, pyrogallol, phloroglycinol, hydroxydiphenyl, bisphenol A, gallic acid, gallic acid ester, α-naphthol, β-naphthol, and the like.

Examples of the aldehydes include formaldehyde, furfural, benzaldehyde, nitrobenzaldehyde, acetaldehyde, and the like.

The catalyst used in the addition condensation reaction, which is not specifically limited, is exemplified by hydrochloric acid, nitric acid, sulfuric acid, formic acid, oxalic acid, acetic acid, etc., in regards to acid catalyst.

The flexibility of the novolak resins can be enhanced still more when o-cresol is used, a hydrogen atom of a hydroxide group in the resins is substituted by other substituents, or bulky aldehydes are used.

The mass average molecular weight [sic] of (D1) novolac resin is not particularly limited as long as the purpose of the present invention is not impaired, but the mass average molecular weight is preferably 1,000 to 50,000.

[(D2) Polyhydroxystyrene Resin]

The hydroxystyrene compound to constitute the (D2) polyhydroxystyrene resin is exemplified by p-hydroxystyrene, α-methylhydroxystyrene, α-ethylhydroxystyrene, and the like.

Among these, the (D2) polyhydroxystyrene resin (C2) is preferably prepared to give a copolymer with a styrene resin. The styrene compound to constitute the styrene resin is exemplified by styrene, chlorostyrene, chloromethylstyrene, vinyltoluene, α-methylstyrene, and the like.

The mass average molecular weight of the (D2) polyhydroxystyrene resin is not particularly limited as long as the purpose of the present invention is not impaired, but the mass average molecular weight is preferably 1,000 to 50,000.

[(D3) Acrylic Resin]

It is preferred that the (D3) acrylic resin includes a structural unit derived from a polymerizable compound having an ether linkage and a structural unit derived from a polymerizable compound having a carboxy group.

Illustrative examples of the polymerizable compound having an ether linkage include (meth)acrylic acid derivatives having an ether linkage and an ester linkage such as 2-methoxyethyl (meth)acrylate, methoxytriethylene glycol (meth)acrylate, 3-methoxybutyl (meth)acrylate, ethylcarbitol (meth)acrylate, phenoxypolyethylene glycol (meth)acrylate, methoxypolypropylene glycol (meth)acrylate, tetrahydrofurfuryl (meth)acrylate, and the like. The polymerizable compound having an ether linkage is preferably, 2-methoxyethyl acrylate, and methoxytriethylene glycol acrylate. These polymerizable compounds may be used alone, or in combination of two or more kinds thereof.

Illustrative examples of the polymerizable compound having a carboxy group include monocarboxylic acids such as acrylic acid, methacrylic acid and crotonic acid; dicarboxylic acids such as maleic acid, fumaric acid and itaconic acid; compounds having a carboxy group and an ester linkage such as 2-methacryloyloxyethyl succinic acid, 2-methacryloyloxyethyl maleic acid, 2-methacryloyloxyethyl phthalic acid and 2-methacryloyloxyethyl hexahydrophthalic acid. The polymerizable compound having a carboxy group is preferably acrylic acid or methacrylic acid. These polymerizable compounds may be used alone, or in combination of two or more kinds thereof.

The mass average molecular weight of the (D3) acrylic resin is not particularly limited as long as the purpose of the present invention is not impaired, but the mass average molecular weight is preferably 30,000 to 800,000.

The content of (D) alkali-soluble resin is such that when the total amount of the (B) resin and the (D) alkali-soluble resin is taken as 100 parts by mass, the content is preferably 0 parts to 80 parts by mass, and more preferably 0 parts to 60 parts by mass. By adjusting the content of the (D) alkali-soluble resin (D) to the range described above, there is a tendency for resistance to cracking to increase, and film loss at the time of development can be prevented.

<(E) Acid Diffusion Control Agent>

In order to improve the resist pattern configuration, the post-exposure delay stability and the like, it is preferred that the photosensitive resin composition further contains an (E) acid diffusion control agent. The (E) acid diffusion control agent is preferably a (E1) nitrogen-containing compound, and an (E2) organic carboxylic acid, or an oxoacid of phosphorus or a derivative thereof may be further included as needed.

[(E1) Nitrogen-Containing Compound]

Examples of (E1) nitrogen-containing compounds include trimethylamine, diethylamine, triethylamine, di-n-propylamine, tri-n-propylamine, tri-n-pentylamine, tri-n-hexylamine, tri-n-heptylamine, tri-n-octylamine, tri-n-nonylamine, tri-n-decylamine, tribenzylamine, diethanolamine, triethanolamine, n-hexylamine, n-heptylamine, n-octylamine, n-nonylamine, n-decylamine, ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, formamide, N-methylformamide, N,N-dimethylformamide, acetamide, N-methylacetamide, N,N-dimethylacetamide, propionamide, benzamide, pyrrolidone, N-methylpyrrolidone, methylurea, 1,1-dimethylurea, 1,3-dimethylurea, 1,1,3,3-tetramethylurea, 1,3-diphenylurea, imidazole, benzimidazole, 4-methylimidazole, 8-oxyquinoline, acridine, purine, pyrrolidine, piperidine, 2,4,6-tri(2-pyridyl)-S-triazine, morpholine, 4-methylmorpholine, piperazine, 1,4-dimethylpiperazine, 1,4-diazabicyclo[2.2.2]octane, and pyridine. These may be used alone, or in combination of two or more kinds thereof.

The (E1) nitrogen-containing compound may be used in an amount typically in the range of 0 to 5 parts by mass, and particularly in the range of 0 to 3 parts by mass, with respect to 100 parts by mass of total mass of the (B) resin and the (D) alkali-soluble resin.

[(E2) Organic Carboxylic Acid or Oxoacid of Phosphorus or Derivative Thereof]

Among the (E2) organic carboxylic acid, or the oxoacid of phosphorus or the derivative thereof, specific preferred examples of the organic carboxylic acid include malonic acid, citric acid, malic acid, succinic acid, benzoic acid, salicylic acid and the like, and salicylic acid is particularly preferred.

Examples of the oxoacid of phosphorus or derivatives thereof include phosphoric acid and derivatives such as esters thereof such as, e.g., phosphoric acid, phosphoric acid di-n-butyl ester, and phosphoric acid diphenyl ester; phosphonic acid and derivatives such as esters thereof such as, e.g., phosphonic acid, phosphonic acid dimethyl ester, phosphonic acid di-n-butyl ester, phenylphosphonic acid, phosphonic acid diphenyl ester, and phosphonic acid dibenzyl ester; and phosphinic acid and derivatives such as esters thereof such as, e.g., phosphinic acid and phenylphosphinic acid; and the like. Among these, phosphonic acid is particularly preferred. These may be used alone, or in combination of two or more kinds thereof.

The (E2) organic carboxylic acid, or the oxoacid of phosphorus or the derivative thereof may be used in an amount typically in the range of 0 to 5 parts by mass, and particularly in the range of 0 to 3 parts by mass, with respect to 100 parts by mass of total mass of the (B) resin and the (D) alkali-soluble resin.

Moreover, in order to form a salt to allow for stabilization, the (E2) organic carboxylic acid, or the oxoacid of phosphorous or the derivative thereof is preferably used in an amount equivalent to that of the (E1) nitrogen-containing compound.

<(S) Organic Solvent>

The photosensitive resin composition contains an (S) organic solvent. The kind of the (S) organic solvent is not particularly limited as long as the purpose of the present invention is not impaired, and the organic solvent can be appropriately selected for use from the organic solvents that have been conventionally used in positive-type photosensitive resin compositions.

Specific examples of the (S) organic solvent include ketones such as acetone, methyl ethyl ketone, cyclohexanone, methyl isoamyl ketone, and 2-heptanone; polyhydric alcohols and derivatives thereof, like monomethyl ethers, monoethyl ethers, monopropyl ethers, monobutyl ethers and monophenyl ethers, such as ethylene glycol, ethylene glycol monoacetate, diethylene glycol, diethylene glycol monoacetate, propylene glycol, propylene glycol monoacetate, dipropylene glycol and dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, methyl pyruvate, ethylethoxy acetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanate, 3-methoxybutyl acetate and 3-methyl-3-methoxybutyl acetate; aromatic hydrocarbons such as toluene and xylene; and the like. These may be used alone, or as a mixture of two or more kinds thereof.

The content of the (S) organic solvent is not particularly limited as long as the purpose of the present invention is not impaired. When the photosensitive resin composition is used for a thick-film application in which a photosensitive resin layer obtainable by a spin-coating method or the like has a film thickness of 10 μm or greater, it is preferable to use the (S) organic solvent to the extent that the solid concentration of the photosensitive resin composition is 30% to 70% by mass.

<Other Components>

The photosensitive resin composition may further contain a polyvinyl resin for improving plasticity. Specific examples of the polyvinyl resin include polyvinyl chloride, polystyrene, polyhydroxystyrene, polyvinyl acetate, polyvinylbenzoic acid, polyvinyl methyl ether, polyvinyl ethyl ether, polyvinyl alcohol, polyvinyl pyrrolidone, polyvinyl phenol, and copolymers thereof, and the like. The polyvinyl resin is preferably polyvinyl methyl ether in view of lower glass transition temperatures.

Further, the photosensitive resin composition may also contain an adhesive auxiliary agent in order to improve the adhesiveness between a template formed with the photosensitive resin composition and a metal substrate.

Also, the photosensitive resin composition may further contain a surfactant for improving coating characteristics, defoaming characteristics, leveling characteristics and the like. Specific examples of the surfactant include commercially available fluorochemical surfactants such as BM-1000 and BM-1100 (both manufactured by B.M-Chemie Co., Ltd.), Megafac F142D, Megafac F172, Megafac F173 and Megafac F183 (all manufactured by Dainippon Ink And Chemicals, Incorporated), Flolade FC-135, Flolade FC-170C, Flolade FC-430 and Flolade FC-431 (all manufactured by Sumitomo 3M Ltd.), Surflon S-112, Surflon S-113, Surflon S-131, Surflon S-141 and Surflon S-145 (all manufactured by Asahi Glass Co., Ltd.), SH-28PA, SH-190, SH-193, SZ-6032 and SF-8428 (all manufactured by Toray Silicone Co., Ltd.), but not limited thereto.

Additionally, in order to finely adjust the solubility in a developing solution, the photosensitive resin composition may further contain an acid, an acid anhydride, or a solvent having a high boiling point.

Specific examples of the acid and acid anhydride include monocarboxylic acids such as acetic acid, propionic acid, n-butyric acid, isobutyric acid, n-valeric acid, isovaleric acid, benzoic acid, and cinnamic acid; hydroxymonocarboxylic acids such as lactic acid, 2-hydroxybutyric acid, 3-hydroxybutyric acid, salicylic acid, m-hydroxybenzoic acid, p-hydroxybenzoic acid, 2-hydroxycinnamic acid, 3-hydroxycinnamic acid, 4-hydroxycinnamic acid, 5-hydroxyisophthalic acid, and syringic acid; polyvalent carboxylic acids such as oxalic acid, succinic acid, glutaric acid, adipic acid, maleic acid, itaconic acid, hexahydrophthalic acid, phthalic acid, isophthalic acid, terephthalic acid, 1,2-cyclohexanedicarboxylic acid, 1,2,4-cyclohexanetricarboxylic acid, butanetetracarboxylic acid, trimellitic acid, pyromellitic acid, cyclopentanetetracarboxylic acid, butanetetracarboxylic acid, and 1,2,5,8-naphthalenetetracarboxylic acid; acid anhydrides such as itaconic anhydride, succinic anhydride, citraconic anhydride, dodecenylsuccinic anhydride, tricarbanilic anhydride, maleic anhydride, hexahydrophthalic anhydride, methyltetrahydrophthalic anhydride, Himic anhydride, 1,2,3,4-butanetetracarboxylic acid, cyclopentanetetracarboxylic dianhydride, phthalic anhydride, pyromellitic anhydride, trimellitic anhydride, benzophenonetetracarboxylic anhydride, ethylene glycol bis anhydrous trimellitate, and glycerin tris anhydrous trimellitate; and the like.

Furthermore, specific examples of the solvent having a high boiling point include N-methylformamide, N,N-dimethylformamide, N-methylformanilide, N-methylacetamide, N,N-dimethlyacetamide, N-methylpyrrolidone, dimethyl sulfoxide, benzyl ethyl ether, dihexyl ether, acetonyl acetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, phenyl cellosolve acetate, and the like.

Moreover, the photosensitive resin composition may further contain a sensitizer for improving the sensitivity.

<Method of Preparing Chemically Amplified Positive-Type Photosensitive Resin Composition>

The photosensitive resin composition is prepared by mixing the above ingredients by a conventional method and stirring the mixture. Machines which can be used for mixing and stirring the above components include dissolvers, homogenizers, 3-roll mills and the like. After uniformly mixing the above components, the resulting mixture may further be filtered through a mesh, a membrane filter and the like.

<<Method of Manufacturing Substrate with Template>>

There is no particular limitation for the method of forming a resist pattern serving as a template for forming a plated article on a metal surface of a substrate by using the aforementioned photosensitive resin composition. Suitable methods include a method of manufacturing a substrate with a template, comprising
- a lamination step of laminating a photosensitive resin layer comprising a photosensitive resin composition on a metal surface of a substrate,
- an exposure step of irradiating the photosensitive resin layer with an active ray or radiation, and
- a developing step of developing the photosensitive resin layer after the exposure to create a template for forming a plated article.

There is no particular limitation for the substrate on which a photosensitive resin layer is laminated, and conventionally known substrates can be used. Examples include substrates for electronic part, those on which a predetermined wire pattern is formed and the like. One having a metal surface is used as the above substrate, and as metal species constituting a metal surface, copper, gold and aluminum are preferred, and copper is more preferred.

The photosensitive resin layer is laminated on a substrate, for example, as follows. That is, a liquid photosensitive resin composition is applied on a substrate, and then a solvent is removed by heating to form a photosensitive resin layer having a desired film thickness. There is no particular limitation for the thickness of a photosensitive resin layer as long as it can form a resist pattern serving as a template which has a desired film thickness. There is no particular limitation for the film thickness, but it is preferably 10 μm or more, more preferably 10 to 150 μm, in particular preferably 20 to 120 μm, and most preferably 20 to 100 μm.

As a method of applying a photosensitive resin composition onto a substrate, those such as the spin coating method, the slit coat method, the roll coat method, the screen printing method and the applicator method can be used. Pre-baking is preferably performed on a photosensitive resin layer. The conditions of pre-baking may differ depending on the components in a photosensitive resin composition, the blending ratio, the thickness of a coating film and the like, but they are usually about 2 to 60 minutes at 70 to 150° C., preferably 80 to 140° C.

The photosensitive resin layer formed as described above is selectively irradiated (exposed) with an active ray or radiation, for example, an ultraviolet radiation or visible light with a wavelength of 300 to 500 nm through a mask having a predetermined pattern.

Low pressure mercury lamps, high pressure mercury lamps, super high pressure mercury lamps, metal halide lamps, argon gas lasers, etc. can be used as the light source of the radiation. The radiation may include micro waves, infrared rays, visible lights, ultraviolet rays, X-rays, γ-rays, electron beams, proton beams, neutron beams, ion beams, etc. The irradiation dose of the radiation may vary depending on the constituent of the photosensitive resin composition, the film thickness of the photosensitive resin layer, and the like. For example, when an ultra high-pressure mercury lamp is used, the dose may be 100 to 10,000 mJ/cm$^2$. The radiation includes a light ray to activate the (A) acid generator in order to generate an acid.

After the exposure, the diffusion of acid is promoted by heating the photosensitive resin layer using a known method to change the alkali solubility of the photosensitive resin layer at an exposed portion of the photosensitive resin film.

Subsequently, the exposed photosensitive resin layer is developed in accordance with a conventionally known method, and an unnecessary portion is dissolved and removed to form a predetermined resist pattern. At this time, an alkaline aqueous solution is used as a developing solution.

As the developing solution, an aqueous solution of an alkali such as, for example, sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, 1,8-diazabicyclo[5.4.0]-7-undecene or 1,5-diazabicyclo[4.3.0]-5-nonane can be used. Also, an aqueous solution prepared by adding an adequate amount of a water-soluble organic solvent such as methanol or ethanol, or a surfactant to the aqueous solution of the alkali can be used as the developing solution.

The developing time may vary depending on the constituent of the photosensitive resin composition, the film thickness of the photosensitive resin layer, and the like. Usually, the developing time is 1 to 30 min. The method of the development may be any one of a liquid-filling method, a dipping method, a paddle method, a spray developing method, and the like.

After development, it is washed with running water for 30 to 90 seconds, and then dried with an air gun, an oven and the like. As described above, a substrate having a resist pattern serving as a template on a metal surface of a substrate can be manufactured.

Method of Manufacturing a Plated Article

A conductor such as a metal may be embedded, by plating, into a non-resist section (a portion removed with a developing solution) in the template formed by the above method on the substrate to form a plated article, for example, like a contacting terminal such as a bump or a metal post. Note that there is no particular limitation for the method of plate processing, and various conventionally known methods can be used. As a plating liquid, in particular, a solder plating liquid, a copper plating liquid, a gold plating liquid and a nickel plating liquid are suitably used. Finally, the remaining template is removed with a stripping liquid and the like in accordance with a conventional method.

According to the above method, a resist pattern serving a template will be formed while suppressing footing. By using a substrate having a template that is manufactured as described above and in which footing is suppressed and, a plated article having excellent adhesiveness to the substrate can be manufactured.

EXAMPLES

Below, the present invention will be described in more detail with reference to Examples, but the present invention shall not be limited to these Examples.

Examples 1 to 11 and Comparative Examples 1 to 3

In Examples and Comparative Examples, a compound represented by the following formula was used as (A) an acid generator.

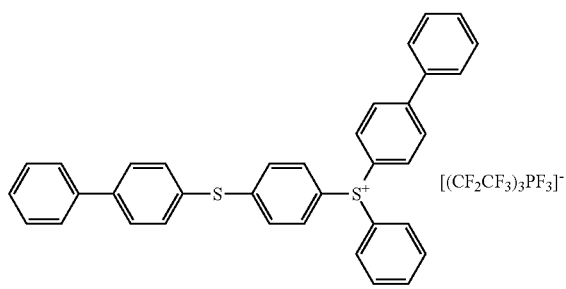 [SMILES: c1ccc(-c2ccc(Sc3ccc([S+](c4ccccc4)c4ccc(-c5ccccc5)cc4)cc3)cc2)cc1]

In Examples and Comparative Examples, resin B-1 (n/m/l/o/p=20/35/20/5/20 [mass ratio], mass average molecular weight [Mw] 40,000, Mw/Mn=2.6) or resin B-2 (n/m/l/o/p=20/35/20/5/20 [mass ratio], mass average molecular weight [Mw]40,000, Mw/Mn=2.6) obtained by copolymerizing the following monomers was used as a resin that, under an action of the (B) acid, undergoes an increase in solubility in alkali. In each of the resins, n to p represent contents (in mass %) of respective constituent units in each of the resins.

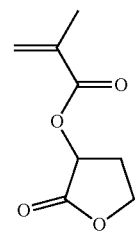 n

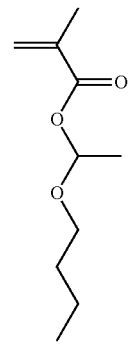 m

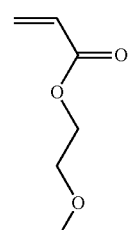 l

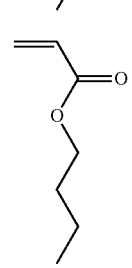 o p

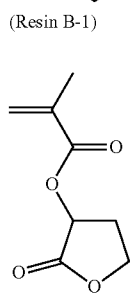

(Resin B-1)

n

-continued

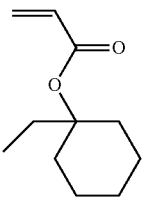

m

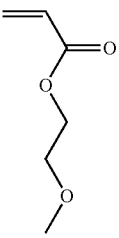

l

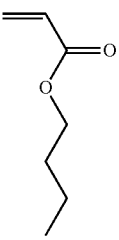

o

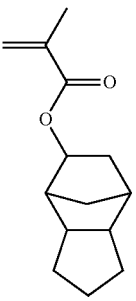

p (Resin B-2)

In Examples and Comparative Examples, the following resin D-1 and D-2 were used as the (D) alkali soluble resin.

D-1: Polyhydroxystyrene resin (p-hydroxystyrene/styrene=85/15 (by mass ration), mass average molecular weight 2,500, Mw/Mn=2.4)

D-2: a novolak resin (a novolak resin obtained by mixing m-cresol and p-cresol in m-cresol/p-cresol=60/40 (by mass ratio), and performing addition condensation in the presence of formaldehyde and an acid catalyst (mass-average molecular weight 8000))

In Examples and Comparative Examples, the following, C-1, C-2, or C-3 was used as the (C) fluorene compound. In the following formula, a compound wherein $A^1$ and $A^2$ represent a hydroxynaphthyl group is C-1, a compound wherein $A^1$ and $A^2$ represent a hydroxyphenyl group is C-2, and a compound wherein $A^1$ and $A^2$ represent an acryloyloxynaphthyl group is C-3. In Comparative Example 1, the fluorene compound was not added to the photosensitive compound.

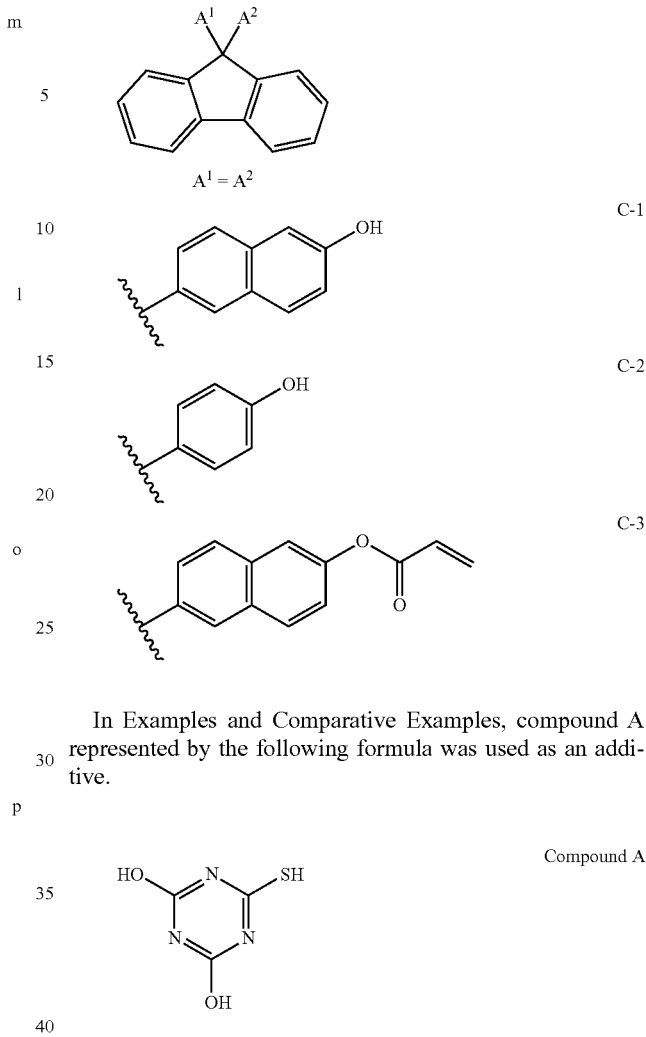

In Examples and Comparative Examples, compound A represented by the following formula was used as an additive.

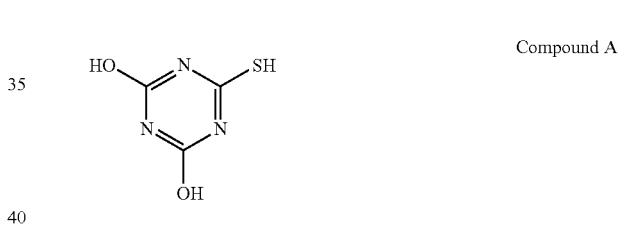

Compound A

Resins and fluorene compounds of the type and amount specified in Table 1, and 2.0 parts by mass of an acid generator, 0.03 part by mass of tri-n-decylamine, and 0.05 part by mass of compound A were dissolved in a solvent of 3-methoxybutyl acetate (MA)/butyl acetate (BA)=5/5 (mass) to a solid content of 50% by mass to obtain photosensitive resin compositions of respective Examples and Comparative Examples.

[Evaluation of Sectional Shape of Non-Resist Section]

The photosensitive resin compositions of the Examples and Comparative Examples were coated by a spin coater on an 8-inch substrate having a surface sputtered with copper to form a photosensitive resin layer having a film thickness of 50 μm. The photosensitive resin layer was prebaked at 130° C. for 5 min. After prebaking, the pattern was exposed to an I radiation of NA 0.50 with a mask having a hole pattern. The substrate was then subjected to post-exposure baking (PEB) at 85° C. for 3 min. The substrate was then developed with a 2.38% aqueous tetramethylammonium hydroxide (TMAH). Thereafter, the developed substrate was washed with running water to obtain a thick-film resist pattern having a contact hole pattern with a diameter of 40 μm.

<Criteria for Evaluation of Sectional Shape>

The sectional shape of the hole pattern was observed under a scanning electron microscope (SEM) and was visually evaluated.

A: The sectional shape was substantially rectangular.

B: The sectional shape was not rectangular.

[Depth of Focus (DOF) Margin]

In EOP in which a hole pattern is formed, the depth of focus was properly vertically shifted, and a resist pattern was formed in the same manner as described above to determine the width (μm) of focal depth that can allow a rectangular pattern to be formed.

<Criteria for Evaluation of Sectional Shape>

A: The width of depth of focus is not less than 5 μm.

B: The width of depth of focus is less than 5 μm.

TABLE 1

| | Resin | | | | Fluorene compound | | | |
|---|---|---|---|---|---|---|---|---|
| | B-1 | D-1 | D-2 | B-2 | Type | Parts by mass | Shape | DOF |
| Example 1 | 100 | — | — | — | C-1 | 15 | A | A |
| Example 2 | 80 | 20 | — | — | C-1 | 15 | A | A |
| Example 3 | 40 | 20 | 40 | — | C-1 | 15 | A | A |
| Example 4 | 80 | 20 | — | — | C-2 | 15 | A | A |
| Example 5 | 80 | 20 | — | — | C-3 | 15 | A | A |
| Example 6 | 80 | 20 | — | — | C-1 | 20 | A | A |
| Example 7 | — | 20 | — | 80 | C-2 | 15 | A | A |
| Comparative Example 1 | 80 | 20 | — | — | — | — | B | B |

It was found from Table 1 that, for the Examples where a fluorene compound was contained, both the sectional shape of the non-resist section of the obtained resist pattern and the depth of focus (DOF) margin were superior to those in Comparative Example 1 where a fluorene compound was not contained.

Specifically, it was found from Comparative Example 1 and Examples 2, 4, and 5 that both the sectional shape of the non-resist section of the obtained resist pattern and the depth of focus (DOF) margin were excellent even when the type of the fluorene compound was varied.

It was found from Examples 2 and 6 that both the sectional shape of the non-resist section of the obtained resist pattern and the depth of focus (DOF) margin were excellent even when the content of the fluorene compound was varied.

It was found from Examples 2 and 3 that, when the composition contained a fluorene compound, both the sectional shape of the non-resist section of the obtained resist pattern and the depth of focus (DOF) margin were excellent even when the type of the resin incorporated was varied.

What is claimed is:

1. A photosensitive resin composition comprising: an (A) acid generator; a (B) resin; and a fluorene compound, wherein the (A) acid generator, when irradiated with an active ray or radiation, generates an acid, the (B) resin, under action of an acid, undergoes an increase in solubility in alkali, wherein the fluorene compound in the photosensitive resin composition consists essentially of (C) a fluorene compound is represented by the formula (1):

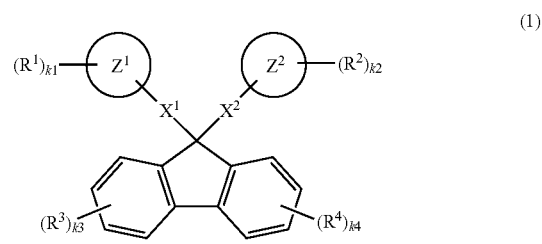

wherein each of ring $Z^1$ and ring $Z^2$ independently represents a benzene ring or a naphthalene ring; each of $X^1$ and $X^2$ independently represents a single bond or —S—; each of $R^1$ and $R^2$ independently represents a hydroxyl group or a (meth)acryloyloxy group; each of $R^3$ and $R^4$ independently represents a monovalent hydrocarbon group, a hydroxyl group, a (meth)acryloyloxy group, a group represented by —$OR^{4a}$, a group represented by —$SR^{4b}$, an acyl group, an alkoxycarbonyl group, a halogen atom, a nitro group, a cyano group, a mercapto group, a carboxy group, an amino group, a carbamoyl group, a group represented by —$NHR^{4c}$, a group represented by —$N(R^{4d})_2$, a sulfo group, or a group in which at least a part of the hydrogen atoms bonded to a carbon atom contained in a monovalent hydrocarbon group, a group represented by —$OR^{4a}$, a group represented by —$SR^{4b}$, an acyl group, an alkoxycarbonyl group, a group represented by —$NHR^{4c}$, or a group represented by —$N(R^{4d})_2$ is substituted by a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxy group, an amino group, a carbamoyl group, a group represented by —$NHR^{4c}$, a group represented by —$N(R^{4d})_2$, a (meth)acryloyloxy group, a mesyloxy group, or a sulfo group; each of $R^{4a}$ to $R^{4d}$ independently represents a monovalent hydrocarbon group; k1 and k2 represent 1; and each of k3 and k4 independently represents an integer of 0 to 4.

2. The photosensitive resin composition according to claim 1, further comprising an (D) alkali soluble resin.

3. The photosensitive resin composition according to claim 2, wherein the (D) alkali soluble resin comprises at least one selected from the group consisting of a (D1) novolak resin, a (D2) polyhydroxystyrene resin and an (D3) acrylic resin.

4. The photosensitive resin composition according to claim 1, wherein each of the ring $Z^1$ and ring $Z^2$ represents a benzene ring.

5. The photosensitive resin composition according to claim 1, further comprising an (S) organic solvent.

6. A method of manufacturing a substrate with a template, the method comprising:

forming a photosensitive resin layer by coating the photosensitive resin composition according to claim 1 in liquid form on a metal surface of a substrate and removing a solvent;

irradiating the layer with an active ray or radiation; and developing the exposed layer to form a template for forming a plated article.

7. The method according to claim 6, wherein the photosensitive resin composition further comprises an (D) alkaline soluble resin.

8. The method according to claim 7, wherein the (D) alkaline soluble resin comprises at least one selected from the group consisting of a (D1) novolak resin, a (D2) polyhydroxystyrene resin and an (D3) acrylic resin.

9. The method according to claim 6, wherein each of the ring $Z^1$ and ring $Z^2$ represents a benzene ring in the (C) fluorene compound included in the photosensitive resin composition.

10. A method of manufacturing a plated article, the method comprising:
    plating non-resist sections on the substrate with the template manufactured by the method according to claim 6 to form the plated article within the template, and removing the remaining template to form the article.

11. The method according to claim 10, wherein the photosensitive resin composition further comprises an (D) alkaline soluble resin.

12. The method according to claim 11, wherein the (D) alkaline soluble resin comprises at least one selected from the group consisting of a (D1) novolak resin, a (D2) polyhydroxystyrene resin and an (D3) acrylic resin.

13. The method according to claim 10, wherein each of the ring $Z^1$ and ring $Z^2$ represents a benzene ring in the (C) fluorene compound included in the photosensitive resin composition.

14. A photosensitive resin composition comprising; an (A) acid generator, a (B) resin, and a fluorene compound, wherein
    the (A) acid generator, when irradiated with an active ray or radiation, generates an acid, the (B) resin, under action of an acid, undergoes an increase in solubility in alkali, wherein
    the flurorene compound in the photosensitive resin composition consists of a (C) fluorene compound represented by formula (1) below:

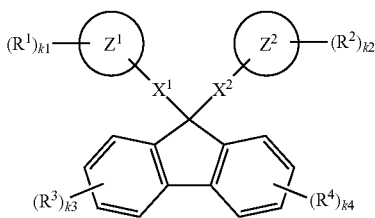

(1)

wherein each of ring $Z^1$ and $Z^2$ independently represents a benzene ring or a naphthalene ring; each of $X^1$ and $X^2$ independently represents a single bond or S; each of $R^1$ and $R^2$ independently represents a hydroxyl group or a (meth)acryloyloxy group; each of $R^3$ and $R^4$ independently represents a monovalent hydrocarbon group, a hydroxyl group, a (meth)acryloyloxy group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a sulfo group, or a group in which at least a part of the hydrogen atoms bonded to a carbon atom contained in a monovalent hydrocarbon group, a group represented by —$OR^{4a}$, a group represented by —$SR^{4b}$, an acyl group, an alkoxycarbonyl group, a group represented by —$NHR^{4c}$ or a group represented by —$N(R^{4d})_2$, is substituted by a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a mesyloxy group, or a sulfo group; each of $R^{4a}$ to $R^{4d}$ independently represents a monovalent hydrocarbon group; k1 and k2 represent 1; and each of k3 and k4 independently represents an integer of 0 to 4.

15. The photosensitive resin composition according to claim 14, wherein each of the ring $Z^1$ and ring $Z^2$ represents a benzene ring.

16. The photosensitive resin composition according to claim 14, further comprising an (S) organic solvent.

17. The photosensitive resin composition according to claim 14, wherein the photosensitive resin composition further comprises an (D) alkaline soluble resin.

18. The photosensitive resin composition according to claim 17, wherein the (D) alkaline soluble resin comprises at least one selected from the group consisting of a (D1) novolak resin, a (D2) polyhydroxystyrene resin and an (D3) acrylic resin.

* * * * *